(12) United States Patent
Schwind et al.

(10) Patent No.: US 7,745,228 B2
(45) Date of Patent: *Jun. 29, 2010

(54) DEVICE FOR SIMULTANEOUSLY CARRYING OUT BLOOD GROUP DETERMINATION, SERUM CROSS-CHECK AND ANTIBODY DETECTION TEST

(75) Inventors: Peter Schwind, Fribourg (CH); Klemens Löster, Bergfelde (DE)

(73) Assignee: Medion Diagnostics AG, Bonnstrasse (CH)

( * ) Notice: Subject to any disclaimer, the term of this patent is extended or adjusted under 35 U.S.C. 154(b) by 206 days.

This patent is subject to a terminal disclaimer.

(21) Appl. No.: 10/563,681
(22) PCT Filed: Jul. 8, 2004
(86) PCT No.: PCT/EP2004/007525
§ 371 (c)(1), (2), (4) Date: Jun. 21, 2006
(87) PCT Pub. No.: WO2005/005986
PCT Pub. Date: Jan. 20, 2005

(65) Prior Publication Data
US 2007/0042499 A1 Feb. 22, 2007

(30) Foreign Application Priority Data
Jul. 9, 2003 (DE) ................................. 103 30 981

(51) Int. Cl.
*G01N 33/53* (2006.01)
(52) U.S. Cl. ........................ 436/164; 436/514; 436/518; 436/512; 436/808; 436/810; 435/287.1; 435/287.7; 435/970
(58) Field of Classification Search ................. 436/514, 436/518, 512, 808, 810; 435/287.1, 287.7, 435/970
See application file for complete search history.

(56) References Cited

U.S. PATENT DOCUMENTS 4,943,522 A 7/1990 Eisinger et al.

(Continued)

FOREIGN PATENT DOCUMENTS

CA 2047637 2/1992

(Continued)

OTHER PUBLICATIONS

USPTO Office Action dated May 18, 2009 issued for U.S. Appl. No. 10/563,659.

*Primary Examiner*—Bao-Thuy L Nguyen
(74) *Attorney, Agent, or Firm*—RatnerPrestia

(57) ABSTRACT

This invention relates to a device for the simultaneous qualitative or quantitative determination of several analytes in a liquid sample. The device comprises a membrane with a charging zone, for the application of the liquid sample, at least two indicator zones which can interact with the analyte(s) and at least one absorption region, which accepts the fluid after passing through the indicator zones, whereby the indicator zones lie between the charging zone and an absorption region, characterized in that the flow directions (flow tracks) are essentially parallel from the application zone through each indicator zone to an absorption region and at least two different flow tracks are present. The invention further relates to a method for the determination of several analytes or derivatives thereof in a liquid sample, comprising: application of the sample to the charging zone of a membrane of the device, whereby said sample is present in sufficient amounts to permit the sample fluid to flow in the direction of the absorption region through the indicator zones and to permit the analytes or derivatives thereof in the liquid sample to form a complex in the indicator zone.

16 Claims, 4 Drawing Sheets

U.S. PATENT DOCUMENTS

| | | | |
|---|---|---|---|
| 5,424,220 A | 6/1995 | Goerlach-Graw et al. | |
| 5,559,041 A * | 9/1996 | Kang et al. | 436/518 |
| 5,770,458 A * | 6/1998 | Klimov et al. | 436/518 |
| 5,869,252 A | 2/1999 | Bouma et al. | |
| 5,962,215 A | 10/1999 | Douglas et al. | |
| 6,100,099 A | 8/2000 | Gordon et al. | |
| 6,103,536 A | 8/2000 | Geisberg | |
| 6,203,757 B1 | 3/2001 | Lu et al. | |
| 6,372,515 B1 | 4/2002 | Casterlin et al. | |
| 6,855,561 B2 * | 2/2005 | Jerome et al. | 436/514 |
| 7,303,923 B2 * | 12/2007 | Hardman et al. | 436/518 |
| 2002/0110803 A1 | 8/2002 | Dhar et al. | |
| 2003/0040021 A1 | 2/2003 | Clark et al. | |
| 2003/0045001 A1 | 3/2003 | Burgess et al. | |

FOREIGN PATENT DOCUMENTS

| | | |
|---|---|---|
| DE | 199 06 005 | 1/2000 |
| EP | 0223978 | 6/1987 |
| RU | 2 124 729 C1 | 1/1999 |
| WO | WO 88/03650 | 5/1988 |
| WO | WO 88/08534 * | 11/1988 |
| WO | WO 94/23299 | 10/1994 |
| WO | WO 94/23300 | 10/1994 |
| WO | WO 94/29696 | 12/1994 |
| WO | WO 97/31268 | 8/1997 |
| WO | WO 97/34148 | 9/1997 |

* cited by examiner

DEVICE FOR SIMULTANEOUSLY CARRYING OUT BLOOD GROUP DETERMINATION, SERUM CROSS-CHECK AND ANTIBODY DETECTION TEST

CROSS-REFERENCE TO RELATED APPLICATIONS

This application is a U.S. National Phase Application of PCT International Application PCT/EP2004/007525, filed Jul. 8, 2004, incorporated herein by reference, which claims priority on German Patent Application DE 103 30 981.0, filed Jul. 9, 2003.

FIELD OF THE INVENTION

The invention relates to a device for lateral-diagonal flow multi-parameter tests, in particular in the fields of immune hematology and of infection serology, for the simultaneous, qualitative or quantitative determination of a plurality of analytes in a liquid sample, including at least one membrane with an application zone for the application of the liquid sample, at least two indicator zones which are able to interact with the analyte(s) and at least one absorption region which absorbs the liquid after having passed the indicator zones, the indicator zones being positioned between the application zone and the absorption region, characterized in that the directions of flow from the application zone through the respective indicator zones to the absorption region (flow tracks) are essentially parallel and there being present at least two different flow tracks.

The invention further relates to a process for analyzing a plurality of analytes in a liquid sample, comprising applying the sample onto the application zone of a membrane of the apparatus according to the invention, wherein this sample is present in adequate quantity in order to induce the sample liquid to flow in the direction of the adsorption region through the indicator zones and in order to induce the analytes or their derivatives in the sample liquid to form a complex in the indicator zones, in particular for the simultaneous determination of cellular and plasmatic parameters, preferably for the simultaneous conduction of blood group determination and serum cross-check (serum reverse regrouping) and/or antibody detection tests as well as for simultaneously conducting blood group determinations and the determination of transfusion relevant infection serological markers as well as for the simultaneous conduction of blood group determination and the determination of antibodies which are directed against blood cells other than erythrocytes, in particular anti-thrombocytes and anti-lymphocytes antibodies.

BACKGROUND OF THE INVENTION

In order to prevent risks of complications, e.g. during a transfusion, in particular blood group incompatibilities, viral and/or bacterial contaminations it is known to perform a variety of laboratory tests on the donor and patient blood in order to make available components which are compatible in a blood group serological sense with the recipient and are free of known transmittable pathogens. The respective serological tests as a rule include the determination of the blood group of the donor and the recipient, in particular of blood groups of the blood group systems ABO, Rh and Kell, serum cross-checks on the donor and recipient, antibody detection tests in respect of irregular antibodies of the donor and recipient as well as antibody identifications in the case of the recipient where irregular antibodies are present. The detection of antibodies against thrombocytes and or lymphocytes is performed likewise in the context of transfusions and transplantations.

Infection serological tests on the donor include in a known manner the routine determination of antibodies, in particular against HIV-I, HIV-II, against HCV against treponema pallidum (syphilis), as well as the determination of the hepatitis B surface antigen (=HbsAg: hepatitis surface antigen).

In blood group serological diagnostics, parameters are generally tested which are of particular relevance in the context of transfusions or of morbus haemolyticus neonatorum (Mhn). This includes inter alia the detection of antigens on the surface of erythrocytes which are characteristic for the blood groups (blood group determination). Further important antigen systems are present also on thrombocytes, granulocytes, lymphocytes which likewise play a role in the context of transfusions and transplantations. In the event of thrombocytes and granulocytes antigen non-identity between mother and fetus pathological symptoms may occur with neonatants comparable with Mhn. In addition the detection of regular blood group antibodies (isoagglutinine) and of irregular blood group antibodies in serum or plasma is applicable here.

The isoagglutinines or regular antibodies are acquired particularly by humans soon after their birth and correspond to the respective blood group of the ABO system. They are directed against those blood group antigens A or B which the individual itself lacks, i.e. persons which have the blood group A have anti-B, persons of blood group B have anti-A persons of blood groups O have anti-A and anti-B; persons of blood group AB have no isoagglutinine. The regular antibodies are also known as "complete" because they are able to directly agglutinate erythrocytes in NaCl medium.

The irregular or allo-antibodies, in contrast to the isoagglutinines are acquired by immunizations in later life, in particular by transfusion or pregnancy. For that reason most humans have no irregular blood group antibodies. The transfusion relevant irregular antibodies are as a rule heat reactive and belong mostly to the IgG class. In contrast to the regular antibodies they are not able to directly agglutinize erythrocytes in a NaCl medium.

It is known that for determining blood groups the erythrocytes of the persons to be tested, (donors or recipients) are brought together with reagents which contain blood group specific antibodies. Generally these tests are performed in the liquid state, in which by mixing of an erythrocyte containing sample with a sample containing antibodies directed against a specific blood group characteristic a testing batch is produced. The testing batch is then incubated over a defined period and under defined conditions and after conclusion of the incubation, either directly or after a centrifugation step, is tested visually or by optical methods for a possible agglutination or adsorption of the erythrocytes. The predominant end point measurement in blood group serology is still the hemaglutination test. For each blood group to be determined a separate batch must be pipetted, i.e. e.g. for the determination of the nine most important blood groups A, B, D, C, c, E, e, Cw and K, nine separate batches are needed, without counting any control.

For the serum cross-check cell reagents with known ABO blood groups (A1, A2, B, 0) are used in a known manner which are incubated with the serum or plasma of the person to be tested. After a centrifugations step a possible agglutination of the erythrocytes is tested for visually or by optical methods. For a serum cross-check with the aforesaid test cells it is conventionally necessary to pipette four batches.

In order to search for irregular antibodies panels are generally used comprising two or three blood group O cells the combined antigen profile of which contains the most important antigens, in particular the blood group systems Rh, Kell, Duffy, Kidd, MNS, P, Lewis, Lutheran. The cell reagent is brought together with the serum or plasma of the person to be tested, is incubated and after a step of centrifugation is tested visually or by optical methods for any agglutination of the erythrocytes. Two to three batches must be pipetted for testing one patient sample.

In order to identify the irregular antibodies which as a rule takes place after a positive antibody detection test, panels comprising up to 16 blood group O cells are used the antigen profile of which covers the most important antigens, in particular the blood group systems Rh, Kell, Duffy, Kidd, MNS, P, Lewis, Lutheran in an exactly predetermined manner. The cell reagent is brought together with the serum or blood plasma of the person to be tested and by visual or optical methods is tested for any agglutination of the erythrocytes. For testing a patient sample up to 16 batches must be pipetted.

Because most transfusion relevant irregular antibodies are of the IgG type and are therefore incomplete the reactions for antibody detection and identification as described must as a rule be reinforced in order to be able to detect the end point of the hemaglutination. The most common reagent for this purpose is a polyclonal anti-humanglobulin reagent to which frequently anti-complement antibodies have been added (typically anti-C3d and/or anti-C3b).

A commonly used method for detecting thrombocyte antibodies is the so-called MAIPA test (monoclonal antibody immobilization of platelet antigens). In this case test thrombocytes are incubated with the serum to be tested. After a rinsing step, incubation is performed with a monoclonal, e.g. mouse antibody which is specific for a particular thrombocyte glycoprotein. The thrombocytes are thereafter subjected to lysing and the diluted lysate is introduced into a reaction vessel coated e.g. with goat anti-mouse antibodies of a microtitration panel. The goat anti-mouse antibody binds the mouse antibody and the thrombocyte glycoprotein human antibody complex attached thereto. The human antibody is tested for by the addition of an enzyme-conjugated goat anti-human IgG.

With conventional diagnostic tests it is possible only to either determine cellular or plasmatic parameters. In order to determine blood components it is invariably necessary to first separate cells from plasma.

Lateral flow tests nowadays are frequently applied as quick tests e.g. as pregnancy tests, for determining infection markers or for drug screening. A lateral flow test device in a known manner includes a rigid support on which an application zone for the sample to be tested is provided, a separating membrane, on which bonding elements, e.g. catcher antibodies or antigens are bound and on which the bonding reactions can be detected, and a suction generating absorption region which causes the sample to be tested to flow in a linear manner through the separating membrane.

Test membranes of conventional lateral flow tests are generally described involving a chromatography-like separation. The analyte in the sample binds specifically to the bonding elements fixed in a membrane which as a rule are present in consecutive or superimposed bands serving as indicator zones. The binding complex is rendered visible by indicator particles which as a rule are already present in the device in dehydrated form in a conjugate liberation pad. The conjugate liberation pad is provided between the application zone and the membrane. The pre-coated colored indicator particles are coated for example with an antibody directed against the analyte to be tested for.

The conventional lateral flow test format corresponds to a so-call "sandwich assay", in which both the indicator zone as well as the indicator particles are coated with a ligand aimed at the analyte tested for, normally an antibody. In that context the ligand (bonding element) is immobilized on the membrane. The detector reagent, normally an antibody bonded to a colored polystyrene particle or to colloidal metals, is deposited in the conjugate liberation pad in a leachable manner. This bonding complex serves as indicator particle. Once the sample to be tested has been applied it very rapidly wets the conjugate liberation pad, whereby the indicator particles are mobilized. The indicator particles migrate with the liquid front along the porous membrane. An analyte present in the sample becomes bonded by the antibody coupled to the indicator particle. As the sample passes the indicator zone, the analyte/indicator particle complex in the indicator zone is immobilized by reaction of the analyte with the antibody bonded in the indicator zone, resulting in a visible signal.

A further known test format for small analytes comprising but a single antigenic determinant, incapable of simultaneously bonding two antibodies, is the so-called "competition assay". The detector reagent bonded to the indicator particle is normally a molecule identical to or analogous with the analyte. The indicator particles are deposited in the conjugate liberation pad. The indicator particles migrate with the liquid front along the porous membrane. If the sample contains the analytes, and if the indicator particles (which effectively likewise contain analyte) pass the indicator zone, part of the analyte molecules in the sample bond to part of the indicator particles. The more analyte is present in the sample the more effective will it compete with the bonding of the indicator particle and the weaker will the signal become.

According to the prior art these indicator particles are predominantly composed of colloidal gold or of polystyrene, manufactured and coated according to methods known to the skilled person. In the typical lateral flow tests formats the analytes are determined indirectly. In this context a direct determination of an analyte denotes that the analyte is already bonded naturally to the indicator particle (e.g. erythrocyte). In the more common situation of indirect determination of the analytes the sample to be tested as a rule contains a non-cellularly bonded, e.g. plasmatic component as the analyte and, besides the sample to be tested, two reagent components are required, i.e. indicator particles and a bonding element. In the indirect determination the analyte initially bonds to the indicator particle dissolved out of the conjugate liberation pad, before this complex becomes immobilized in the indicator zones with the bonding element by way of a second reaction.

When using conventional lateral flow tests with erythrocytes as indicator particles which have been bonded to the analytes to be determined, for example blood group specific antigens, it is at present usual for antibodies to be provided in the indicator zones against corresponding blood group antigens serving as bonding elements in successive or superimposed bands in but a single flow track such as for example anti-A, anti-B against the Rh blood group system. In this context conventional lateral flow tests suffer from the disadvantage that the erythrocytes bonded to the antibodies form a flow barrier against the analytes still to be tested for, for example further cell associated antigens, in a sample. Due to agglutination or adsorption of cells in a band of bonding elements arranged proximally to the application zone, additional analytes, in particular cells or cell fragments in the sample to be tested, can no longer be separated unimpededly and visibly and can therefore not be tested for unambiguously or completely. For example in a person who is blood group AB Rh D positive this may result in a weakening or elimination of the B and the D bands, which may result in a faulty interpretation of being blood group A Rh negative. For that reason it was hitherto not possible, specifically in blood group serological diagnostics to employ a lateral flow test with more than one indicator zone. In order to determine a plurality of, in particular cellular and plasmatic blood group parameters, it is to date necessary to conduct single parameter tests separately.

SUMMARY OF THE INVENTION

It is an object of the invention to overcome the disadvantages referred to of the state-of-the-art, in particular of the successive or superposed indicator or testing zones of conventional lateral flow tests for a simultaneous determination of different sample parameters, in particular of cellular and plasmatic parameters.

The object is attained according to the invention on the one hand by a device for the simultaneous qualitative or quantitative determination of one or more analytes in a liquid sample or a plurality of liquid samples comprising at least one membrane with an application zone for applying the liquid sample, at least one group of at least two indicator zones which can enter into interaction with the analyte(s) or with which analytes can interact and an absorption region which takes up the liquid after having passed the indicator zones, wherein the indicator zones are positioned between the applications zone and the absorption region characterized in that the flow directions from the applications zone through the respective indicator zones of a group towards an absorption region, representing flow tracts are substantially parallel, there being present at least two different flow tracks.

The indicator zones of the apparatus according to the invention are present on the membrane and comprise bonding elements which capture or bond the analytes to be determined in the sample. The bonding reactions between the analyte and the bonding element are detected in the indicator zones. Antibodies or antibody fragments, lectines, antigens or antigen epitopes and/or cells or cell fragments are fixed to the porous membrane as particularly preferred bonding elements. The indicator zones preferably each comprise one bonding element against one analyte to be tested for.

In an embodiment of the invention the indicator zones are so arranged that the sample liquid for each flow track will flow through not more than one indicator zone. For example, the indicator zones are provided on the membrane in staggered relationship.

This arrangement of the indicator zones is, in this context, preferably configured in a row extending diagonally from proximal to distal or vice versa. Particular embodiments are V-shaped, W-, M- or N-shaped or reversed V-shaped W-, M- or N-shaped. In a further embodiment the indicator zones are staggered parallel side by side in a linear row.

The provision of staggered indicator zones is a precondition for a multi-parameter testing with erythrocytes as indicator particles in a lateral arrangement. The particularly preferred embodiment of a diagonal arrangement offers the advantage that the denotation of the results can be applied to the device according to the invention in a particularly practical and easily readable manner; because each parameter to be tested for occupies a defined X and Y position the arrangement of the device according to the invention can be considered as a coordinate system having an ordinate (plane of the direction of flow) and an abscissa (plane of the application zone).

In a further embodiment of the invention more than one such rows of indicator zones, extending preferably each from proximal to distal or vice versa in a diagonal direction or for example even V-shaped, W-, M- or N-shaped or reversed V-shaped W-, M- or N-shaped, extending in the direction of flow sequentially and/or laterally staggered, and the indicator zones of the various rows are either arranged in spaced apart relationship so that the sample liquid for each flow track flows through not more than a single indicator zone or extend in contact with one another such that the sample liquid for each flow track flows through more than one indicator zone.

More than one such row of indicator zones, for example two rows of indicator zones having different distances from the application zone are particularly advantageous in the event that from a complete blood sample cellular and plasmatic parameters are to be determined. In one embodiment, for example in a test batch containing complete blood as sample, the bonding elements are so selected that the analytes contained in the plasma, for example any kind of antibodies, which flow through the apparatus from the application zone to the adsorption region through the indicator zones, become bonded to the bonding elements in the row of indicator zones arranged proximally to the application zone. The bonding elements for detecting the cellularly bonded analytes, for examples erythrocyte antigens, are, on the other hand, so selected that these become bonded to the bonding elements in that row of indicator zones which is arranged distally to the application zone. In this preferred embodiment one preferably operates, in addition to the erythrocytes, with a further type of indicator particle, preferably of colloidal gold or polystyrene or with immobilized erythrocytes. These indicator particles are employed in particular in order to render visible in the bonding complex in an indicator zone analytes which are not bonded to erythrocytes, for example antibodies occurring freely in plasma. If for example two types of indicator particles are employed one of which is not erythrocytes, the indicator zones of the two rows can be arranged side by side in contact with one another or sequentially in a single flow tract. In this context the arrangement is advantageous in which the analytes to be tested for in plasma are detected in the proximal indicator zones and where the erythrocytes-bonded analytes are detected in the distal indicator zones. An embodiment of the invention comprising more than one row of indicator zones as aforesaid in which the bonding elements of each row react or bond to erythrocytes serving as indicator particles, the rows of indicator zones are in spaced apart interrelationship or in a single flow tract and not in succession.

In a further and particularly preferred embodiment of the invention more than one such row of indicator zones are provided preferably in one row extending diagonally from proximal to distal or vice versa or for example in a row extending in a V-shaped, W-, M- or N-shaped manner or reversed V-shaped, W-, M- or N-shaped row or even for example in a row extending parallel side by side in staggered relationship, bi-directionally (e.g. at an angle of 180° to one another) in relation to a central application zone. Such an arrangement is advantageous in particular in the event that from a complete blood sample cellular and plasmatic parameters are to be detected.

In an embodiment for example in a test batch comprising complete blood as the sample, the bonding elements are so selected that the analytes contained in the plasma, for example any type of antibodies which flow from the application zone to the absorption region through the indicator zones, become bonded to the bonding elements in the row of indicator zones provided on the one side of the application zone. The bonding elements for detecting the cellularly bonded analytes, for example erythrocyte antigens, are on the other hand so selected that these become bonded to the bonding elements of the end row of indicator zones arranged on the opposite side of the application zone. In the case of this preferred embodiment one preferably operates, in addition to the erythrocytes, with a further kind of indicator particles, preferably of colloidal gold or polystyrene. These indicator particles are employed in particular in order to render visible in the bonding complex in an indicator zone, analytes which are not bonded to erythrocytes, for example antibodies occurring freely in the plasma.

In a preferred embodiment the one application zone furthermore comprises two different membranes of differing porosaties. In this preferred embodiment one preferably operates, in addition to the erythrocytes, with a further kind of indicator particles, preferably of colloidal gold or polystyrene. These indicator particles are particularly employed in order to render visible in the bonding complex in an indicator zone analytes which are not bonded to erythrocytes, for example antibodies occurring freely in plasma.

In a particularly preferred embodiment the one application zone includes a membrane or two different membranes of differing porosities. Furthermore, one of the membranes includes a conjugate pad arranged between a sealing element and indicator zones. In this preferred embodiment one preferably operates in addition to the erythrocytes with a further kind of indicator particles, particularly of colloidal gold or polystyrene. The indicator particles are employed in particular in order to render visible in the bonding complex in an indicator zone analytes which are not bonded to erythrocytes, for example antibodies occurring freely in the plasma. This further kind of indicator particles, employed in addition to the erythrocytes, is preferably present in dried form in the conjugate pad. Furthermore the conjugate pad takes care that the flow of erythrocytes is slowed down. This has the affect that in the bi-directional arrangement including a single common application zone optimized conditions are maintained in the one direction for detecting cellular properties and in the opposite direction optimized conditions are maintained for the detection of plasmatic properties.

By means of the device according to the invention a lateral flow test, in particular for blood serological diagnostics is made available by means of which erythrocytes can be used as indicator particles and wherein in a single test batch simultaneously several cellular parameters, in particular erythrocyte antigens or antigen epitopes, plasmatic parameters and/or blood cell properties, in particular of complete blood components can be determined in each sample to be tested. Moreover, in this manner a test system is made available which can be manufactured particularly easily and can be employed in particular with few test series and without sample preparation, as well as being cost-effective, but by means of which simultaneously a variety of cellular parameters and/or plasmatic parameters of a sample or a plurality of samples to be tested can be determined.

The device according to the invention affords these advantages in all medical diagnostic fields in which simultaneously different cellular parameters and plasmatic parameters are to be determined, in particular also in the field of blood group and infections serology, in particular in the context of any diagnostics relevant to transfusion medicine, e.g. for the simultaneous conductance of blood group determinations wherein in particular erythrocytes bonded antigens or antigen epitopes are determined and for serum cross-checking, wherein in particular regular antibodies (isoagglutinines) are determined and/or antibody detection tests, wherein in particular irregular antibodies are determined, for example for the simultaneous conduction of blood group determinations and the detection of transfusion relevant infection serological markers, for example antibodies against HIV-I, HIV-2, HCV, treponema pallidum, as well as the surface antigen of hepatitis B virus (HbsAg) as well as for the simultaneous conduction of blood group determinations and the detection of antibodies against other blood cells such as erythrocytes in particular anti-thrombocyto and anti-lymphocyto antibodies.

In this context anti-coagulation treated or native complete blood can be used, where it is not necessary, prior to the testing to extensively separate from one another erythrocytes and serum or plasma fractions. The determination may be performed in a manual format, i.e. completely without instruments (including electric current).

In a preferred embodiment of the device according to the invention the indicator zones include, preferably in a row of indicator zones arranged distally to the application zone, antibodies or antibody fragments or lectines which capture or bind the blood group antigens to be determined of all conceivable blood group systems and accordingly the cells serving as their carriers, present in the sample. Antibodies or antibody fragments or lectines against antigens or antigen epitopes, in particular of the blood group systems ABO, Rh and Kell, for example anti-A, anti-B, anti-D and anti-K are applied as preferred bonding elements in the indicator zones on the porous membrane, preferably in a row distal to other indicator rows.

Preferably a control bonding element (control=ctl) is applied in an indicator zone of this row of indicator zones, preferably in an indicator zone distal to all remaining indicator zones of this row, which gives a positive indication of the flow of the samples through the indicator zones. The control bonding element is preferably a polyclonal anti-erythrocyte antibody.

This preferred embodiment of the device according to the invention comprises in a further row of indicator zones, preferably arranged proximally to the application zone, antigens or antigen epitopes which capture or bond the regular antibodies in the sample. For this purpose, serving as preferred bonding elements, A1, A2, B, O blood group antigens or antigen epitopes, for example erythrocyte membranes of erythrocytes of defined blood groups (A1, A2, B, O) or synthetically produced blood group substances are applied to the porous membrane. Preferably, in an indicator zone of this row of indicator zones, preferably in an indicator zone distal to all remaining indicator zones of this row, a control bonding element (control=ctl) is applied which positively indicates the flow of the sample through the indicator zones. The control bonding element is preferably an anti-IgG antibody.

This preferred embodiment of the device according to the invention can in a further row of indicator zones, preferably proximal to the application zone, comprise antigens or antigen epitopes which capture or bond the irregular antibodies or fragments thereof in the sample. As preferred bonding elements for this purpose the cell membranes of different blood group O erythrocyte preparations, the combined antigen profile of which covers those antigens which are directed against the important transfusion relevant irregular antibodies, are fixed onto the porous membrane. Preferably a control bonding element (control=ctl) which positively indicates the flow of the sample through the indicator zones is applied in an indicator zone of this row of indicator zones, preferably in an indicator zone distal to all remaining indicator zones of this row. The control bonding element is preferably an anti-IgG antibody.

In a further preferred embodiment of the device according to the invention the indicator zones, preferably in a row of indicator zones arranged distally to the application zone, comprise antibodies or antibody fragments or lectines which capture or bond the blood group antigens to be determined in the blood group determination, and thereby the cells in the sample which carry those antigens. Antibodies or antibody fragments or lectines against antigens or antigen epitopes of the ABO blood group system, for example anti-A, anti-B, anti-A and anti-B are fixed to the porous membrane in the indicator zone serving as preferred bonding elements, preferably in a row arranged distally to the application zone and to other indicator zone rows.

Preferably a control bonding element (control=ctl) which positively indicates the flow of the sample through the indicator zones is provided in an indicator zone of this row of indicator zones, preferably in an indicator zone which is distal to all remaining indicator zones of this row. The control bonding element is preferably a polyclonal anti-erythrocyte antibody.

This preferred embodiment of the device according to the invention comprises in a further row of indicator zones which is preferably proximal to the application zone, thrombocytes and/or lymphocytes membranes or membrane components serving as bonding elements for the detection of anti-thrombocyte/lymphocyte antibodies.

In a further preferred embodiment of the device according to the invention, the indicator zones, preferably in a row of indicator zones distal to the application zone, comprise antibodies or antibody fragments or lectines which capture or bond the blood group antigens to be determined for the blood group determinations and thereby also the cells in the sample which carry the aforegoing. Antibodies or antibody fragments or lectines against antigens or antigen epitopes of the ABO blood group system, for example anti-A, anti-B, anti-A and anti-B are affixed as preferred bonding elements to the porous membrane in the indicator zones, preferably in a row which is distal to the application zone and to other indicator zone rows.

Preferably in an indicator zone of this row of indicator zones, preferably in an indicator zone which is distal to all remaining indicator zones of this row, a control bonding element (control=ctl) is applied which positively indicates the flow of the sample through the indicator zone. The control bonding element is preferably a polyclonal anti-erythrocyte antibody.

This preferred embodiment of the device according to the invention comprises in a further row of indicator zones, preferably arranged proximally to the application zone, bonding elements for the detection of infective agents, in particular synthetically produced peptides or the recombinant antigens expressed with recombinant DNA methods, and which include diagnostically significant sequences of surface proteins of the respective markers (antibody detection) or antibodies which are directed against (surface) proteins of infective agents (antigen detection).

As a result of the device according to the invention it is no longer necessary for the simultaneous determination of cellular and plasmatic parameters of a sample to perform separate pipetting for each individual determination, but rather all desired parameters can be determined simultaneously in a sample particularly in the case of simultaneous performance of blood group determinations and serum cross-checking and/or antibody detection tests as well as in the simultaneous conduction of blood group determinations and determinations of transfusion relevant infection serological markers, wherein it is possible to combine the blood group determination with the detection of any infection serological marker, as well as in the simultaneous performance of blood group determinations and determination of antibodies against blood cells other than erythrocytes, in particular anti-thrombocyte and anti-lymphocyte antibodies.

This represents an exceptional rationalization of the procedures. Besides the advantage of simultaneous determination of many serological parameters, the virtually complete redundancy of sample preparations as compared with conventional tests should be mentioned. The reading of the results represented in a diagonal pattern is likewise more advantageous. Thus, in the device according to the invention it is possible, for example, to determine and read in a device, side by side, for example blood groups in particular ABO properties and serum cross-checks and antibody detection tests or blood group in particular ABO properties and other immune hematological parameters in particular anti-thrombocyte and/or anti-lymphocyte antibodies or fragments thereof or blood group in particular ABO properties and infection serological markers, in particular antibodies against bacterial and/or viral agents or fragments thereof or viral or bacterial antigens or epitopes.

The two-dimensional planar display as well as the stable end point of the reaction, facilitate not only reading with the naked eye but also the automatic reading of the results with conventional display analytical methods, such as e.g. CCD cameras. The work expenditure is reduced even where manual evaluation is performed. The device according to the invention moreover results in a reduction of environmental impact and in favorable cost affects. Even in emergency situations under time pressure it is, for example, possible to perform in a short period in a single test device, a complete ABO blood group determination with serum cross-checks and antibody detection test for irregular antibodies, for example a complete ABO blood group determination with infection serological marker determination or anti-thrombocyte/lymphocyte antibody determination. From a production technical point of view the lateral-diagonal flow pattern offers considerable advantages compared with the state-of-the-art, involving a considerably reduced consumption of reagents employed and in view of the provision of a multiplicity of test parameters in a single device which previously had to be tested for separately.

Due to the device according to the invention a lateral flow test, in particular for immune hematological and infection serological diagnostics is provided by means of which in a single testing batch simultaneously several cellular, in particular erythrocytal antigens or antigen epitopes, plasmatic parameters and/or blood cell properties, in particular of complete blood components can be determined per sample being tested, there being employed at least two kinds of indicator particle of which at least one kind is represented by erythrocytes. In addition, there is thereby made available a cost-effective test system, easily produceable which can be handled in the simplest possible manner with few test runs and without sample preparation by means of which simultaneously different cellular parameters and/or plasma parameters of a sample in particular blood group characteristics, detection of regular and irregular antibodies against thrombocytes and/or lymphocytes and/or infection serological markers in particular those with transfusion medicinal relevancy can be determined.

The membrane of the device according to the invention is a porous membrane. Preferred membrane materials are, for example, nitrocellulose (e.g. uniS-art of Sartorius, HiFlow of Millipore, Whatman, AE99 or FF85/100 of Schleicher & Schuell), polyethylene (Lateral Flo of Porex Corporation) or nylon (Novalon of CUNO). Preferably the membrane has the largest possible pore size because a high porosity of the membrane facilitates the influx in particular of cellular components of the sample to be tested e.g. of erythrocytes into the porous structure. The use of absorbent membranes is particularly advantageous. However, the device according to the invention is not limited by such properties. Preferred are all membranes having a high capillary flow rate (capillary speed) wherein the capillary flow rate represents that time which is required by a dye solution in order to travel forty millimeters on a given membrane. Particularly preferred are membranes having a capillary flow rate less than 100.

In the bi-directional embodiment using two different membranes, the one membrane preferably has a higher capillary flow rate, preferably, less than 100, and the other membrane preferably has a lower capillary flow rate, preferably more than 100.

In a preferred embodiment of the invention a sealing element is provided on the porous membrane downstream of the application zone of the device in accordance with the invention. Two- or three-dimensional sealing elements, which are placed onto the porous membrane and by means of which a sample application zone separate from the remaining surface of the porous membrane, are employed. According to the invention the sealing element primarily has the effect of a liquid barrier and permits the directional distribution of sample liquid and test reagents in the porous membrane. Moreover the sealing element according to the invention seals off the sample application zone in order to prevent an inadvertent entry of liquid into the remaining parts of the lateral flow device. Preferred embodiments of the sealing element are web shapes or trough shapes or funnel shapes. The shaping of the sealing element takes place by cutting processes from the material used for the production of the sealing element. In the case of the funnel or trough shape the sealing element is provided with an inner aperture, the preferred modifications of which are round, square or rectangular and tapering towards the underside (membrane contact side) of the sealing element in the case of the funnel shape.

Preferred materials for the sealing element are materials which are hydrophobic. In a special embodiment, the materials are coated on one side with an adhesive film, for example, a pressure sensitive or self-adhesive acrylate adhesive. Accordingly, the sealing element can be adhesively bonded directly onto the surface of the porous membrane. Alternatively, the sealing element can be bonded to the lateral flow casing, for example adhesively bonded such that in this embodiment the lateral flow casing presses the sealing element against the surface of the porous membrane such that the functions of the sealing element are attained.

Preferred materials for the formation of two-dimensional sealing elements are any form of adhesive tape or adhesive foils (e.g. Tesa 4124 of Beiersdorf AG, ARcare 7815 of Adhesives Research).

Preferred materials for the formation of three-dimensional sealing elements are flexible, closed pore elastomer materials or flexible silicon materials of variable material thicknesses, preferably 3-5 mm (e.g. cellular caoutchouk EPDM140 of Pitzner, silicone rubber or solid caoutchouk, hardness 40° or less of Castan).

Due to the structure according to the invention the device according to the invention is capable of accommodating liquid samples which contain cells, for example complete blood without filtering of the cells. Moreover, the sealing element permits the application of large volumes of sample onto the porous membrane (application zone) without flooding thereof. Accordingly the sealing element supports the utilization of the absorbent properties of the porous membrane. Furthermore, the sealing element ensures a directional flow of sample. Nevertheless, the device according to the invention can function well with or without any sealing element.

For the absorption region (absorption pad) of the device according to the invention, mechanically stable materials are preferred, preferably having a water absorption capacity of 20-30 g/100 cm$^2$ (e.g. Wicking Papier, type 300, Schleicher and Schüll). The contact between the absorption pad and the lateral flow membrane of the device according to the invention is produced by contact pressure and overlapping with the porous membrane. The exact positioning of the absorption pad on the membrane is attained by adhesive bonding of the absorption pad to the carrier layer (backing sheet) carrying the lateral flow membrane.

The conjugate pad preferably consists of glass fiber or cellulose and preferably has the property of retarding the flow of native erythrocytes.

In a further embodiment the components of the device according to the invention are applied for purposes of mechanical strengthening onto a support or carrier layer. The device according to the invention can however also function without a carrier layer. Preferably mechanically stable and non-water absorbent materials, preferably having thicknesses of 100 μm or more coated on one or both sides with an adhesive film e.g. a pressure sensitive or self-adhesive acrylate adhesive (e.g. 0.005 inch polyester W/GL-187, G & L). On the carrier layer the porous membrane and the absorption pad are fixed. In the case of a carrier layer rendered adhesive on both sides, the adhesive second side is employed for fixing the stack onto further surfaces, e.g. inside the lateral flow casing.

In a further embodiment the device according to the invention, either with or without a carrier layer, onto which the components of the device according to the invention have been applied, is integrated in a casing, by which the membrane components are pressed onto one another and the casing supports the sealing element function. However, in this context the device according to the invention can function as well with as without a casing.

A further subject of the invention is the use of the device according to the invention for the analysis of blood, in particular for simultaneously performing the blood group determination and serum cross-checking and/or antibody detection test and/or for the simultaneous performance of the blood determination and the detection of antibodies against infectious in particular bacterial and/or viral agents or fragments thereof or of antigens of infective agents and/or for the simultaneous performance of blood group determinations and the detection of antibodies against erythrocytes other than blood cells, in particular anti-thrombocyte and/or anti-lymphocyte antibodies or fragments thereof.

The object is attained according to the invention also by a process for determining a plurality of analytes or their derivatives in a liquid sample comprising the application of the sample onto the application zone of a membrane of the device according to the invention, wherein the sample is present in adequate amount in order to induce the sample liquid to flow in the direction of the absorption region through the indicator zones and in order to induce the analytes or their derivatives in the sample liquid to become bonded to the respective indicator zones or to form a complex in the indicator zones.

A specific embodiment of the process according to the invention performs simultaneously a blood group determination and a serum cross-checking and/or antibody detection tests.

For example complete blood or a diluted form thereof is applied onto the application zone of the device. All components penetrate, guided by the sealing element into the porous membrane and pass during migration in the direction of the absorption pad initially through the indicator zone region for serum retesting, taking up fragments of the cells A1, A2, B, O as well as through the control indicator shown including anti-IgG/IgM. The isoagglutinines present in the serum become bonded to the corresponding cellularly bound antigens. Serum IgG bonds to the control bonding element (serum cross-check: sensibilisation).

The cellular bound antigens migrate onwards into the indicator zone region distal to the indicator zone region for serum cross-checking, for blood group determination wherein in each indicator zone an antibody is immobilized against a different blood group characteristic, (e.g. anti-A, anti-B, anti-AB). The indicator zone of this region most distal to the application zone for example comprises polyclonal anti-erythrite antibodies as a bonding element. In this indicator zone region the erythrocytes become bonded to the bonding elements corresponding to the respective blood group characteristics. Erythrocytes of each and every blood group (blood group determination) become bonded to the control bonding element.

In a subsequent rinsing step non-bonded material is washed from the membrane. In the subsequent detection step immobilized isoagglutinines and control antibodies immobilized on the bonding elements of the proximal series of indicator zones are rendered visible (serum cross-check: detection) by means of synthetic particles coated with anti-IgG/IgM.

In a further embodiment of the process according to the invention for the simultaneous blood group determination and serum cross-check and/or antibody detection test the blood group characteristics are determined directly as described above whereas the serum cross-check and/or antibody detection test is performed as a competition test.

By way of example complete blood or a diluted form thereof is applied onto the application zone of the device. Guided by the sealing element all components penetrate into the porous membrane and pass during their migration in the direction of the absorption pad initially through the indicator zone region for serum cross-checking which comprises fragments of cells of blood group A and B as well as the control indicator zone which comprises fragments of cells of blood group O. The isoagglutinines present in the serum become bonded to the corresponding cellularly bound antigens (serum cross-check: sensibilisation).

The cellularly bound antigens migrate onwards into the indicator zone region for blood group determination located distal to the indicator zone region for serum cross-checking and wherein in each indicator zone an antibody against a different blood group characteristic is immobilized (e.g. anti-A, anti-B, anti-D). The indicator zone of this region which is most distal to the application zone may, for example, have polyclonal anti-erythite anti-bodies serving as bonding element. In this indicator zone region the erythrocytes become bonded to those bonding elements which correspond to the respective blood group characteristics. Erythrocytes of whatever blood group bond to the control bonding element (blood group determination).

In the subsequent rinsing step, non-bonded material is rinsed out of the membrane. In the next following step a suspension of different synthetic particles, coated respectively with anti-A, anti-B or anti-H is applied onto the application zone. The particles are only able to bond each to that bonding element in the indicator zone region for serum cross-checking which during the sensibilisation step had not been brought into contact with the serum isoagglutinines i.e. displaying a colored band which in this case indicates the absence of the corresponding isoagglutinines. For example in the case of a blood group A (persons having isoagglutinines anti-B) the cell fragments of the B cells are blocked by the isoagglutinines which results in the cell fragments of the A cells becoming stained by the subsequently applied mixture of synthetic particles due to the anti-A particles contained therein. The blood group O fragments are stained in all conceivable constellations because they are not blocked by isoagglutinines and are accordingly always free to react with the stained anti-H particles, as a result of which a control element is also made available in the modification of a competition assay (serum cross-check: detection).

In a further embodiment of the process according to the invention for simultaneous blood group determination and serum cross-checking and/or antibody detection test including direct determination of the blood group characteristics and determination of the serum cross-check and/or antibody detection test performed as a competition test, the following procedure is followed.

Complete blood or a diluted form thereof is applied onto the asymmetrical application zone of the device having two different porous membranes. One of the porous membranes has a lower capillary flow rate than the other membrane. In the case of the latter, a conjugate pad containing dried anti-A/anti-B/anti-H particles has been applied onto the membrane between the sealing element and the indicator zones. Guided by the sealing element, all components penetrate into both porous membranes, resulting in the following flow characteristics:

"Membrane only side": All components during their migration pass in the direction of the associated absorption pad through the indicator zone region for blood group determination in which in each indicator zone there is provided an antibody against a different blood group characteristic in immobilized form (e.g. anti-A, anti-B, anti-D). The indicator zone of this region most distal to the application zone comprises for example polyclonal anti-erythrocyte antibodies as a bonding element. In this indicator zone region the erythrocytes become bonded to those bonding elements which correspond to the respective blood group characteristics. Erythrocytes of whatever blood group become bonded to the control bonding element.

"Membrane/conjugate pad side": All components having penetrated into the membrane and passed the sealing element enter into contact with the conjugate pad causing the cellular components to be retained or retarded whereas the liquid components (plasma) can flow onward without restraint. The latter cause the anti-A/anti-B/anti-H particles to be released from the conjugate pad. The indicator zone region of the serum cross-check includes fragments of cells of the blood groups A and B as well as control element fragments of cells of the blood group O. The isoagglutinines present in serum become bonded to the corresponding cellularly bound antigens and compete thereby for bonding of the stained anti-A, anti-B particles. This means that the particles can bond only if the respective isoagglutinine is absent. For example, a blood group A person has anti-B isoagglutinines which results in the blood group B fragments being blocked in the indicator zone region so that only the blood group A fragments can be stained by the colored anti-A particles. The control element against which no isoagglutinines exist accordingly always remains unblocked and becomes stained as a visible band by the anti-H particles contained in the particle mixture of the conjugate pad.

A further particular embodiment of the process according to the invention results simultaneously in a blood group determination and a determination of anti-thrombocyte and/or anti-lymphocyte antibodies or fragments thereof.

By way of example for the determination of the anti-thrombocyte antibodies the indicator zones in the region proximal to the application zone includes thrombocyte fragments as bonding elements to which—if present in the sample—anti-thrombocytal antibodies contained in the serum will become bonded. The remainder of the process is as described in the preceding embodiment of the process according to the invention, in particular the blood group determination proceeds as there described.

A further particular embodiment of the process according to the invention performs simultaneously a blood group determination and a determination of transfusion relevant infection serological markers.

By way of example, for the determination of infection markers, the indicator zones of the first proximal indicator zone region include as bonding elements synthetic peptides and/or recombinant proteins corresponding to the sequences of proteins of viral or bacterial agents, (determination of antibodies against infection markers, e.g. anti-HIV-1), as well as antibodies which are directed against infection markers (determination of antigens e.g. HbsAg). Antibodies or antigens as the case may be contained in the serum bond in the first step to the corresponding antigens or antibodies. The remainder of the process is as described in the preceding embodiment of the process according to the invention, in particular the blood group determination proceeds as there described.

In the process according to the invention the analytes to be determined more particular represent blood group antigens or antigen epitopes, preferably those of the blood group systems ABO, Rh, Kell in order to interact with blood group antigens or with antigen epitopes against antibodies or fragments thereof preferably regular antibodies, irregular antibodies in order to detect antibodies against infective agents (surface) antigens of infective agents and/or anti-thrombocytol or anti-lymphocytol antibodies or fragments thereof.

The sample to be inspected for example native or anticoagulated complete blood or erythrocyte concentrates or diluted erythrocyte suspensions, blood components or test liquids such as control serum or control cells is applied onto the application zone of the device according to the invention. The erythrocytes contained in the sample and which carry the analyte(s) at the same time serve as indicator particles.

In particular two groups of indicator particles are used. One thereof is represented exclusively by erythrocytes for the direct detection of erythrocyte-bound analytes. The other group is composed of particles of any conceivable type and combination by means of which bonding reactions can be demonstrated, preferably particles of colloidal gold or of polystyrene or immobilized erythrocytes. In a preferred embodiment different indicator particles are used in each test run, of which at least one type represents native erythrocytes.

BRIEF DESCRIPTION OF THE DRAWINGS

In the following the invention will be further illustrated by figures and examples without being limited thereby.

DETAILED DESCRIPTION OF THE INVENTION

Figure 1:
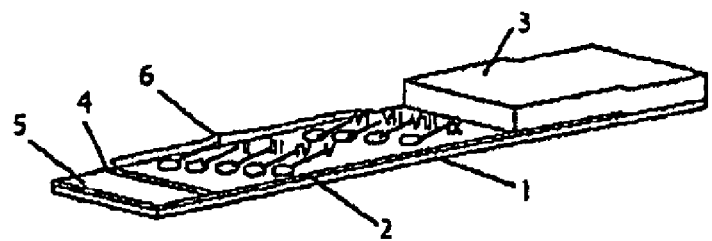
FIG. 1 is a perspective view of a device according to the invention for lateral flow tests for the simultaneous performance of blood group determination and serum cross-checking.

FIG. 1 shows by way of example a perspective illustration of a device according to the invention for lateral flow tests for the simultaneous performance of blood group determinations and serum cross-checking. In the present example the device comprises a support layer 1, the porous membrane 2 the absorption pad 3 and the two-dimensional sealing element 4 in the form of a strip. The porous membrane 2 is fixed onto the support layer 1 by means of a pressure sensitive acrylic adhesive. Likewise, the absorption pad 3 is fixed onto the support layer 1, part of the absorption pad 3 overlapping the porous membrane 2. The sealing element 4 fixed on the upper side of the porous membrane 2 separates the application zone 5 from the remaining membrane surface and permits the directed distribution of sample liquid and test reagents into the porous membrane 2. Between the application zone 5 and the region of the porous membrane 2 which is in contact with the absorption pad 3 the indicator zone region 6 is provided. The latter is formed by diagonally staggered point-shaped indicator zones I-IX arranged in defined X and Y positions wherein the indicator zones I-V denote the indicator zone region "serum cross-check" and the indicator zones VI-IX denote the indicator zone region "blood group determination" and are composed of the following bonding elements:

| Indicator Zone | Bonding Element | Specification |
|---|---|---|
| Indicator zone region: serum cross-check | | |
| I | Erythrocyte ghosts | Blood group A1 |
| II | Erythrocyte ghosts | Blood group A2 |
| III | Erythrocyte ghosts | Blood group B |
| IV | Erythrocyte ghosts | Blood group O |
| V | Antibodies | Anti-human IgG/IgM |
| Indicator zone region: Blood group determination | | |
| VI | Antibodies | Anti-A (monoclonal) |
| VII | Antibodies | Anti-AB (monoclonal) |
| IX | Antibodies | Anti-erythrocytes (polyclonal) |

Indicator zone V is the control (ctl) for the serum cross-check and contains anti-human IgG/IgM antibodies. Indicator zone X is the control (ctl) for the blood group determination and contains polyclonal anti-erythrite antibodies. They are positioned distally to all remaining indicator zones.

Figure 2:
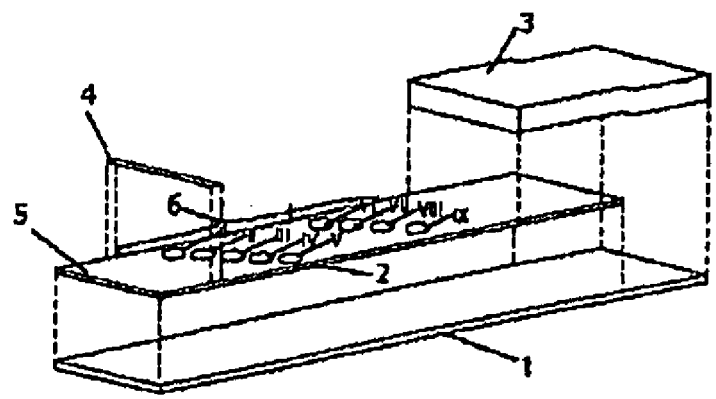
FIG. 2 is an explosive view of the device for lateral flow tests according to the invention illustrated in FIG. 1.

In FIG. 2 an explosive view of the device according to the invention for lateral flow tests illustrated in FIG. 1 is shown comprising the components support layer 1, porous membrane 2, absorption pad 3 and sealing element 4 which separate the application zone 5 from the remainder of the membrane which in turn comprises the indicator zone regions "serum cross-check" and "blood group determination" including the diagonally staggered indicator zones I-IX.

Figure 3:
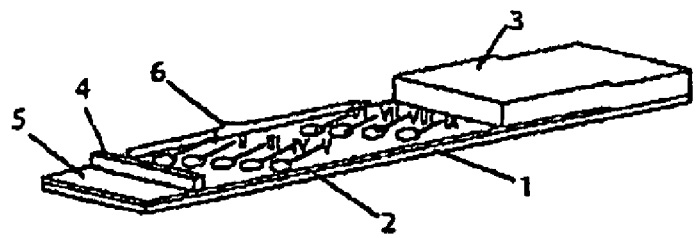
FIG. 3 is a perspective view of a device according to the invention for lateral flow tests for the simultaneous performance of blood group determinations and serum cross-checking carried out with a three-dimensional sealing element in the form of a web.

In FIG. 3 a perspective view of a device according to the invention for lateral flow tests for the simultaneous performance of blood group determinations and serum cross-checks is shown. In the present example the components of the device correspond to the components of the device illustrated in FIG. 1 except for the sealing element fixed to the upper side of the porous membrane 2 in the form of a three-dimensional batten 4.

Figure 4:
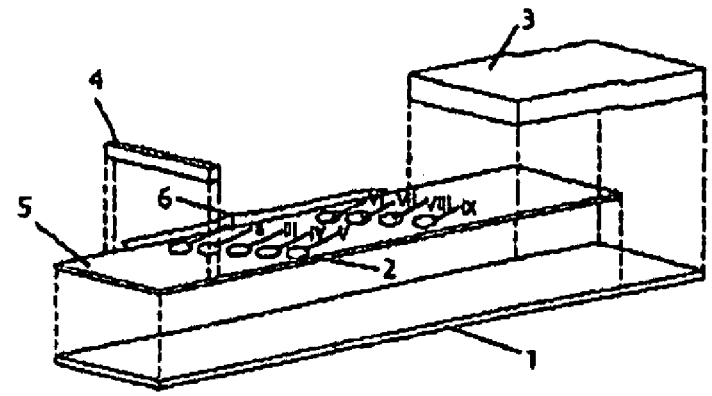
FIG. 4 is an explosive view of the device according to the invention for lateral flow tests illustrated in FIG. 3.

In FIG. 4 an explosive view is shown of the device according to the invention illustrated in FIG. 3 for lateral flow tests including the components support layer 1, porous membrane 2, absorption pad 3 and a sealing element 4 in the form of a three-dimensional batten which separates the application zone from the remaining membrane which in turn contains the indicator zone region 6 comprising the indicator zone regions "serum cross-check" and "blood group determination" including the diagonally staggered indicator zones I-IX.

Figure 5:
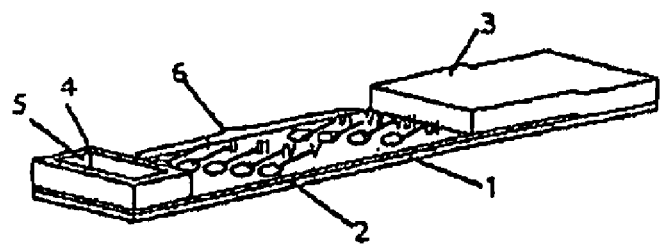
FIG. 5 is a perspective view of a device according to the invention for lateral flow tests for the simultaneous performance of blood group determinations and serum cross-checking performed with a three-dimensional sealing element in the form of a trough.

In FIG. 5 is shown by way of example a perspective illustration of a device according to the invention for lateral flow tests for the simultaneous performance of blood group determinations and serum cross-checking. In the present example the components of the device correspond to the components of the device as illustrated in FIG. 1 except for the sealing element 4 fixed to the porous membrane 2 in the form of a three-dimensional trough.

Figure 6:
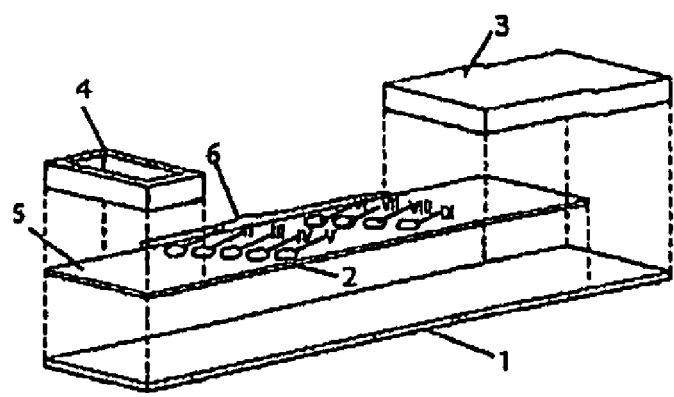
FIG. 6 is an explosive view of the device for lateral flow tests according to the invention illustrated in FIG. 5.

In FIG. 6 an exploded view of the device according to the invention for lateral flow tests illustrated in FIG. 5 is shown including the components support layer 1, porous membrane 2, absorption pad 3 and sealing element 4 in three-dimensional trough form which separates the application zone 5 from the remainder of the membrane which in turn consists of the indicator zone region 6, of the indicator zone regions "serum cross-check" and "blood group determination" including the diagonally staggered indicator zones I-IX.

Figure 7:
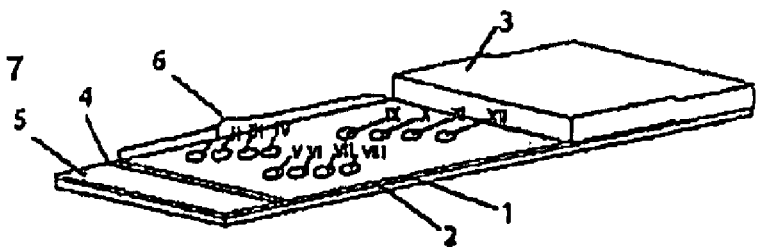
FIG. 7 is a perspective view of a device according to the invention for lateral flow tests for the simultaneous performance of blood group determinations, serum cross-check and antibody detection tests for recipients.

FIG. 7 illustrates by way of example a perspective view of a device according to the invention for lateral flow tests for the simultaneous performance of blood group determinations, serum cross-checking and antibody detection tests for recipients. In the present case the device is composed of a support layer 1, the porous membrane 2, the absorption pad 3 and the two-dimensional sealing element 4 in the form of a strip. The membrane 2 is affixed on the support layer 1 provided with a pressure sensitive acrylic adhesive. Likewise the absorption pad 3 is affixed to the support layer 1 with part of the absorption pad 3 overlapping the porous membrane 2. The sealing element 4 fixed to the upper side of the porous membrane 2 separates the application zone 5 from the remaining membrane surface and permits the directional distribution of sample liquid and test reagents into the porous membrane 2. Between the application zone 5 and the region of the porous membrane 2 which is in contact with the absorption pad 3, the indicator zone region 6 is provided. The latter is formed by diagonally staggered point-shaped indicator zones I-XII provided in defined X and Y positions, the indicator zones I-VIII representing the indicator zone region "serum cross-check/antibodies detection test" and the indicator zones IX-XII representing the indicator zone region "blood group determination" and consists of the following binding elements:

| Indicator Zone | Bonding Element | Specification |
|---|---|---|
| Indicator zone region: serum cross-check/antibody detection | | |
| I | Erythrocyte ghosts | Blood group A1 |
| II | Erythrocyte ghosts | Blood group A2 |
| III | Erythrocyte ghosts | Blood group B |
| IV | Erythrocyte ghosts | Blood group O |
| V | Erythrocyte ghosts | Detector cell 1, blood group O, Rh-formula $R_1$, $R_1^w$ |
| VI | Erythrocyte ghosts | Detector cell 2, blood group O, Rh-formula $R_2$, $R_2$ |
| VII | Erythrocyte ghosts | Detector cell 3, blood group O, Rh-formula $R_1$, $R_1$ |
| VIII | Antibodies | Anti-human IgG/IgM |
| Indicator zone region: Blood group determination | | |
| IX | Antibodies | Anti-A (monoclonal) |
| X | Antibodies | Anti-B (monoclonal) |
| XI | Antibodies | Anti-AB (monoclonal) |
| XII | Antibodies | Anti-erythrocytes (polyclonal) |

Indicator zone VIII is the control (ctl) for the serum cross-check and antibody detection test and contains anti-human IgG/IgM antibodies. Indicator zone XII is the control (ctl) for the blood group determination and contains polyclonal anti-erythrocyte antibodies. It is provided distal to all remaining indicator zones.

Figure 8:
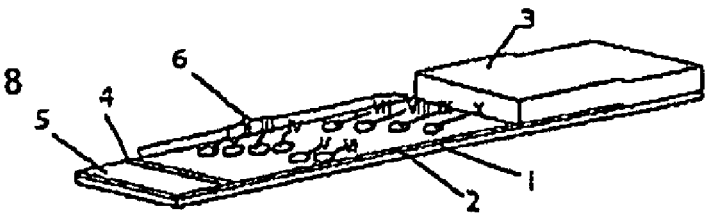
FIG. 8 is a perspective view of a device according to the invention for lateral flow tests for the simultaneous performance of blood group determinations serum cross-checks and antibody detection tests for donors.

In FIG. 8 by way of example, a perspective view of a device according to the invention for lateral flow tests for the simultaneous performance of blood group determinations, serum cross-checking and antibody detection tests for blood donors is shown. In the present example the device comprises a support layer 1, the porous membrane 2, the absorption pad 3 and the two-dimensional sealing element 4 in the form of a strip. The porous membrane 2 is fixed to the support layer provided with a pressure sensitive acrylate adhesive. Likewise the absorption pad 3 is fixed to the support layer 1, part of the absorption pad 3 overlapping with the porous membrane 2. The sealing element 4 fixed on the upper side of the porous membrane 2 separates the application zone 5 from the remaining membrane surface and permits the directed distribution of sample liquid and test reagents into the porous membrane 2. Between the application zone 5 and the region of the porous membrane 2 which is in contact with the absorption pad 3, the indicator region 6 is provided. This is formed by point-shaped indicator zones I-X provided diagonally staggered in defined positions X and Y, the indicator zones I-VI representing the indicator region serum cross-check/antibody detection tests and the indicator zones VII-X comprising the indicator zone region "blood group determination" and being composed of the following bonding elements:

| Indicator Zone | Bonding Element | Specification |
|---|---|---|
| Indicator zone region: serum cross-check/antibody detection | | |
| I | Erythrocyte ghosts | Blood group A1 |
| II | Erythrocyte ghosts | Blood group A2 |
| III | Erythrocyte ghosts | Blood group B |
| IV | Erythrocyte ghosts | Blood group O |
| V | Erythrocyte ghosts | Blood group O, pool of detection cells 1, 2, 3 (see description FIG. 8) |
| VI | Antibodies | Anti-human IgG/IgM |
| Indicator zone region: Blood group determination | | |
| VII | Antibodies | Anti-A (monoclonal) |
| VIII | Antibodies | Anti-B (monoclonal) |
| IX | Antibodies | Anti-AB (monoclonal) |
| X | Antibodies | Anti-erythrocytes (polyclonal) |

Indicator zone VI represents the control (ctl) for the serum cross-check and antibody detection tests and contains anti-human IgG/IgM antibodies. Indicator zone X represents the control (ctl) for the blood group determination and contains polyclonal anti-erythrocyte antibodies. It is situated distally to all remaining indicator cells.

Figure 9:
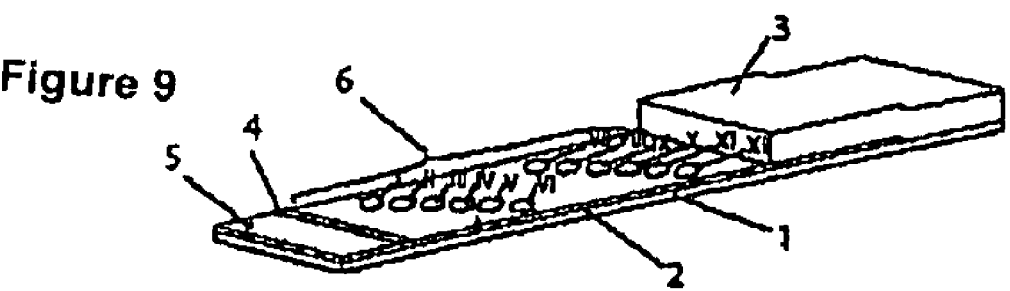
FIG. 9 is a perspective view of a device according to the invention for lateral flow tests for the simultaneous performance of blood group determinations and the detection of infection markers.

In FIG. 9 there is shown by way of example a perspective view of a device according to the invention for lateral flow tests for the simultaneous performance of the blood group determinations and the detection of infection markers. In the present example the device includes a support layer 1, the porous membrane 2, the absorption pad 3 and the two-dimensional sealing element 4 in the form of a strip. The porous membrane 2 is fixed onto the support layer 1 provided with a pressure sensitive acrylate adhesive. Likewise the absorption pad 3 is fixed onto the support layer 1, part of the absorption pad 3 overlapping with the porous membrane 2. The sealing element 4 fixed to the upper side of the porous membrane 2 separates the application zone 5 from the remaining membrane surface and permits the directed distribution of sample liquid and test reagents into the porous membrane 2. Between the application zone 5 and the region of the porous membrane 2 which is in contact with the absorption pad 3 the indicator region 6 is provided. The latter is formed by diagonally staggered point-shaped indicator zones I-XII arranged in defined X and Y positions, the indicator zones I-VI representing the indicator zone "detection of infection markers" and the indicator zones VII-XII the indicator zone region "blood group determination" and are composed of the following bonding elements:

| Indicator Zone | Bonding Element | Specification |
|---|---|---|
| Indicator region: Detection of infection markers | | |
| I | Synthetic peptides | HIV-1 (gp-14, gp-41) |
| II | Synthetic peptides | HIV-2 (gp-36) |
| III | Antibodies | Anti-HBsAg (monoclonal) |
| IV | Recombinant antigen | HCV (C-100, C-200, C33c, C22) |
| V | Recombinant antigen | Syphilis (TpN 15, TpN 17, TpN 47) |
| VI | Antibodies | Anti-human IgG/IgM |
| Indicator zone region: Blood group determination | | |
| VII | Antibodies | Anti-A (monoclonal) |
| VIII | Antibodies | Anti-B (monoclonal) |
| IX | Antibodies | Anti-AB (monoclonal) |
| X | Antibodies | Anti-D (monoclonal) |
| XI | Antibodies | Anti-CDE (monoclonal) |
| XII | Antibodies | Anti-erythrocytes (polyclonal) |

Indicator zone VI is the control (ctl) for the determination of antibodies against infective agents and contains anti-human IgG/IgM antibodies. Indicator zone XII is the control (ctl) for the blood group determinations and contains polyclonal anti-erythrocyte antibodies. It is distally arranged in relation to all other indicator zones.

Figure 10:
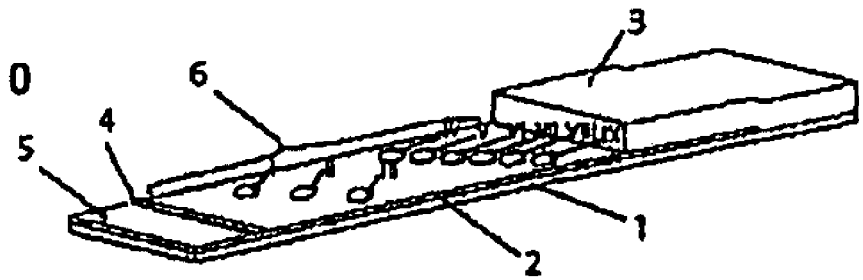
FIG. 10 is a perspective view of a device according to the invention for lateral flow tests for the simultaneous performance of blood group determinations and the detection of antibodies against thrombocytal antigens.

In FIG. 10 a perspective view of a device according to the invention for lateral flow tests is shown by way of example for the simultaneous performance of blood group determinations and the detection of antibodies against thrombocytal antigens. In the present example the device comprises a support layer 1, a porous membrane 2, the absorption pad 3 and the two-dimensional sealing element 4 in the form of a strip. The porous membrane 2 is fixed to the support layer 1 provided with a pressure sensitive acrylate adhesive. Likewise the absorption pad 3 is fixed to the support layer 1, part of the absorption pad 3 overlapping with the porous membrane 2. The sealing element 4 fixed to the upper side of the porous membrane 2 separates the application zone 5 from the remaining membrane surface and permits the directed distribution of sample liquid and test reagents into the porous membrane 2. Between the application zone 5 and the region of the porous membrane 2 which is in contact with the absorption pad 3 the indicator region 6 is provided. This is formed of diagonally staggered point-shaped indicator zones I-IX in defined X and Y positions, wherein the indicator zones I-III include the indicator zone region "detection of antibodies against thrombocytal antigens" and the indicator zones IV-IX the indicator zone region "blood group determination" and consist of the following bonding elements:

| Indicator Zone | Bonding Element | Specification |
|---|---|---|
| Indicator region: Detection of antibodies against thrombocydol antigens | | |
| I | Membrane proteins | Thrombocytes, HPA 1bb3aa5bb |
| II | Membrane proteins | Thrombocytes, HPA 1aa3bb5aa |
| III | Antibodies | Anti-human IgG/IgM |
| Indicator zone region: Blood group determination | | |
| IV | Antibodies | Anti-A (monoclonal) |
| V | Antibodies | Anti-B (monoclonal) |
| VI | Antibodies | Anti-AB (monoclonal) |
| VII | Antibodies | Anti-D (monoclonal) |
| VIII | Antibodies | Anti-CDE (monoclonal) |
| IX | Antibodies | Anti-erythrocytes (polyclonal) |
| XII | Antibodies | Anti-erythrocytes (polyclonal) |

Indicator zone III is the control (ctl) for the detection of antibodies against thrombocytal antigens and contains anti-human IgG/IgM antibodies. Indicator zone IX is the control (ctl) for the blood group determination and contains polyclonal anti-erythrocyte antibodies. It is positioned distally in relation to all remaining indicator zones.

Figure 11:
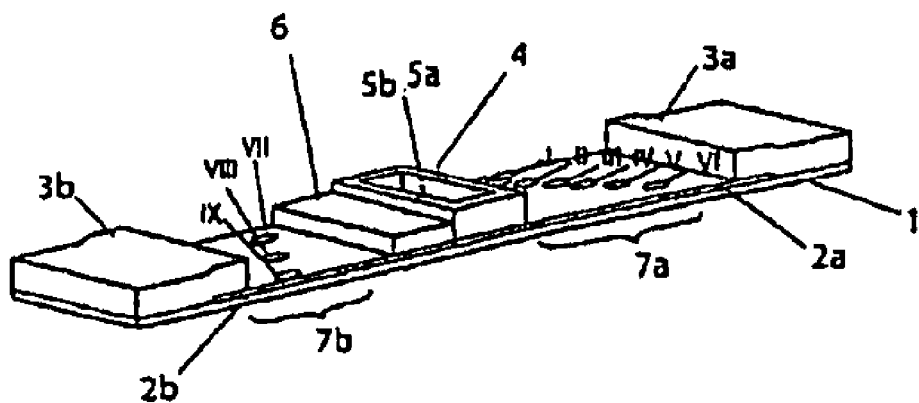
FIG. 11 shows a perspective view of a device according to the invention for lateral flow tests with bi-directional flow for the simultaneous determination of blood group testing and serum cross-checking.

In FIG. 11 is shown by way of example a perspective view of a device according to the invention for lateral flow tests with bi-directional flow for the simultaneous determination of blood groups and serum cross-checks. In the present example the device comprises a support layer 1, a porous membrane 2a for the blood group determination a porous membrane for the serum cross-check which differs from the membrane 2a, the absorption pad 3a and 3b, a three-dimensional sealing element 4 in trough form and a conjugate pad 6. The porous membranes 2a and 2b are fixed onto the support layer 1 provided with a pressure sensitive acrylate adhesive. Likewise the absorption pads 3a and 3b are fixed onto the support layer 1, one part each of the absorption pads 3a and 3b overlapping with the porous membranes 2a and 2b. The sealing element 4 fixed to the upper side of the porous membranes 2a and 2b separates the application zones 5a and 5b respectively from the remaining membrane surfaces and permits the directed distribution of sample liquid and test reagents into the porous membranes 2a and 2b. Between the application zone 5a and the region of the porous membrane 2a with which the absorption pad 3a is in contact, the indicator zone region 7a blood group (blood group determination) is provided. The latter is formed by diagonally staggered point-shaped indicator zones I-VI in defined X and Y positions, the indicator zones of the indicator zone regions 7a consisting of the following bonding elements:

| Indicator Zone | Bonding Element | Specification |
| --- | --- | --- |
| I | Antibodies | Anti-A (monoclonal) |
| II | Antibodies | Anti-B (monoclonal) |
| III | Antibodies | Anti-AB (monoclonal) |
| IV | Antibodies | Anti-D (monoclonal) |
| V | Antibodies | Anti-CDE (monoclonal) |
| VI | Antibodies | Anti-erythrocytes (polyclonal) |

The indicator zone VI represents the control (ctl) for the blood group determination and contains polyclonal anti-erythrocyte antibodies. It is provided distally in respect of the indicator zones I-V.

Between the application zone 5b and the region of the porous membrane 2b which is in contact with the absorption pad 3b the indicator zone region 7b (serum cross-check) is provided. This is formed by point-shaped indicator zones VII-IX, diagonally off-set in defined X and Y positions, the indicator zones of the indicator zone region 7b being composed of the following bonding elements:

| Indicator Zone | Bonding Element | Specification |
| --- | --- | --- |
| VII | Erythrocyte ghosts | Blood group A |
| VIII | Erythrocyte ghosts | Blood group B |
| IX | Erythrocyte ghosts | Blood group O (control) |

Figure 12:
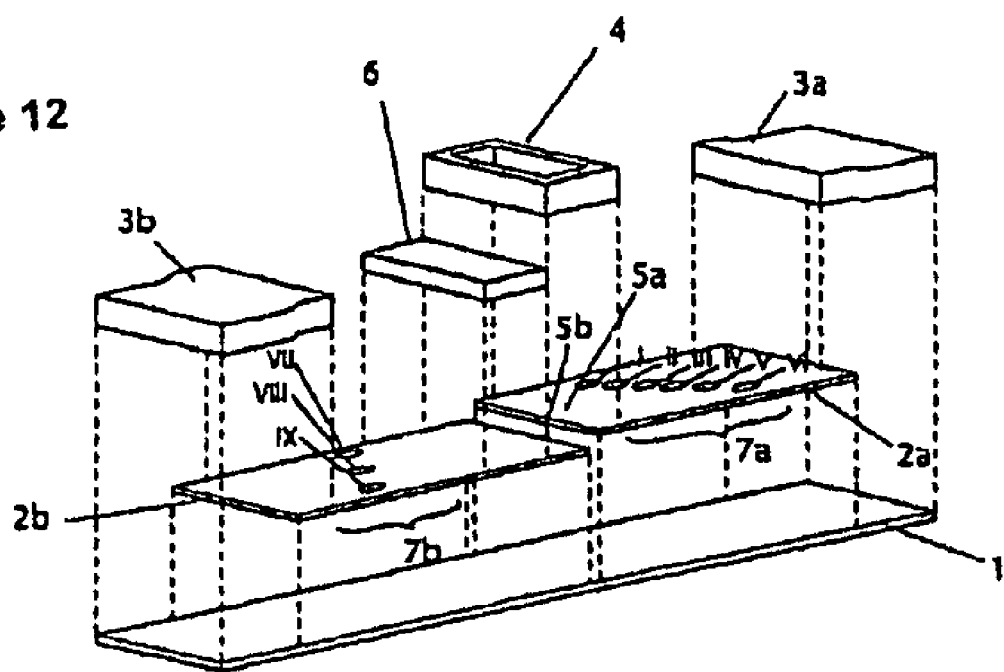
FIG. 12 shows an explosive view of the device according to the invention for lateral flow tests according to FIG. 11.

In FIG. 12 an exploded view is shown of the device according to the invention illustrated in FIG. 1 for lateral flow tests with bi-directional flow composed of the components support layer 1, a porous membrane 2a for the blood group determination, a porous membrane 2b for the serum cross-check which differs from the membrane 2a, the absorption pads 3a and 3b, a three-dimensional sealing element 4 of trough-shaped design and a conjugate pad 6. The sample application zone extends over both porous membranes including the probe application zone 5a of membrane 2a and the probe application zone 5b of membrane 2b and is separated by the sealing element 4 in trough form from the remaining surfaces of the membranes 2a and 2b. The membrane 2a contains the indicator region 7a including the indicator zones I-VI in diagonally staggered arrangement from proximal to distal whereas the membrane 2b contains the indicator region 7b including the indicator zones VII-IX extending from proximal to distal in a diagonally staggered arrangement.

The advantageous properties of this invention can be observed by reference to the following examples, which illustrate but do not limit the invention.

EXAMPLES

Example 1

Simultaneous Blood Group Determination (Direct Assay) and Serum Cross-Check (Direct Binding Assay)

Preparation of Test Strips:

The test strips comprises an application zone an indicator zone region and an absorption region. Membranes of the type Millipore HiFlow Plus 065 are cut to size in strips measuring 15 mm×35 mm (width/length; x/y) and are adhesively bonded onto a support layer (backing sheet, e.g. of G&L). Diagonally staggered 0.2 µl points of the various bonding elements are applied in the indicator zone region divided into the indicator zone region "serum cross-check" (proximal to the application zone) and blood group determination (distal to the application zone):

Indicator zone region "serum cross-check"—suspensions of erythrocyte ghosts of the specification blood group A1, blood group A2, blood group B and blood group O (produced from erythrocyte concentrates) as well as anti-human IgG/IgM antibodies (goat anti-human IgG, goat anti-human IgM, sigma, I-3382, I-0759) as control, indicator zone region "blood group determination"-anti-A, antibodies—clone Birma-1 (serologicals, TLJ0105); anti-B antibodies—clone ES-4 (serologicals, NCA0201); anti-AB antibodies—clones AB6, AB26, AB92 (Medion Diagnostics, 010062); anti-erythrocyte antibodies (rabbit IgG fraction of anti-human RBC, Rockland, 209-4139).

The positioning of the bonding elements of the indictor zone region "serum cross-check" commences with erythrocyte ghosts of the specification blood group A1 in position x=2.5 mm/y=10 mm. All other bonding elements are dispensed iteratively at distances of x=2.5 mm/y=1.5 mm in relation to the position of the erythrocyte ghosts of the specification blood group A1. The erythrocyte ghosts are dispensed as 0.1-0.5% (v/v) suspensions in 15 mM potassium phosphate buffer pH 7.5, 10% (v/v) methanol, the anti-human IgG/IgM antibodies as a 1:1 mixture in a concentration of 50 µg/ml in 15 mM potassium phosphate buffer pH 7.5, 10% (v/v) methanol.

The positioning of the bonding elements of the indicator zone region "blood group determination" starts with the anti-A antibody in position x=3 mm/y=20 mm. All other bonding elements are dispensed iterating at distances of x=3 mm/y=1.5 mm to the position of the anti-A antibody. The dilutions of the antibodies are performed in 15 mM potassium phosphate buffer pH 7.5, 10% (v/v) methanol as follows: anti-A antibody 1:3, anti-B antibody 1:2, anti-AB antibody 1:4, anti-RBC antibody 1:3.

After dispensing the bonding elements the membranes are dried for 20 minutes at 40° C. and subsequently stored at constant air humidity until the test is performed. At the end which is distal to the application zone, an absorption pad sized 15×15 mm (Schleicher and Schüll 300) is adhesively applied onto the membrane overlapping by 3 mm. The application zone is separated over the entire membrane width from the remainder of the membrane by the adhesive application of a 1-2 mm wide adhesive strip (Tesa 4124) in position y=5 mm.

Testing Batch:

For blood samples anti-coagulated complete blood is used. For the test proper 100 µl undiluted or diluted blood 1:3 or 1:6 in diluting buffer (EnlisstII, Medion Diagnostics or Diluent 1, DiaMed) are applied into the application zone. Once the blood has left the application zone rinsing is performed twice with 100 µl EnlisstII in order to remove unbonded erythrocytes from the membrane. Thereafter 50 µl anti-IgG/A/M conjugated gold particles (20 to 40 nm, Arista Biologicals, CGIGA-0800, CGIGG-0800, CGIGM-0800), diluted 1:10 (v/v) in TBS, 0.08% gelatine, 0.5, % albumin are applied onto the application zone. Instead of the gold particles it is also possible to employ colored polystyrene particles of 100 to 400 nm, e.g. of Merck Eurolab France/Estapor. Once the gold particles have left the application zone the membrane is once again rinsed once or twice with 100 µl EnlisstII.

Result:

(a) Controls: The test is valid if the anti-RBC control (indicator zone IX, indicator zone region "blood group determination") displays a clearly positive signal (red dot) and if the anti-IgG/IgM control (indicator zone V, indicator zone region "serum cross-check") is characteristically stained purple (gold particles) or in the color of the polystyrene particles used.

(b) Test Results: Depending on the presence or absence of the respective blood group antigens red dots (positive) or the almost white background coloration of the membrane (negative) is displayed at the corresponding positions in the indicator zone region "blood group determination". The corresponding isoagglutinines can be recognized in the indicator zone region "serum cross-check" by the characteristic purple of the gold particles in the form of purple-shaped dots or in the color of the polystyrene particles used. In the absence of an isoagglutinine no signals differing from background are to be perceived in these positions.

Example 2

Simultaneous Determination of Blood Groups (Direct Assay) and Serum Cross-Check (Competition Assay)

Production of Test Strip:

The test strip consists of an application zone, two indicator zone regions on both sides of the application zone and two absorption regions. Membranes of the type Millipore HiFlow Plus 065 and HiFlow Plus 140 are cut to size into strips sized 15 mm by 20 mm (width/length; x/y) and bonded adhesively side by side onto a support layer (backing sheet e.g. of G&L). Onto the HiFlow Plus 140 membrane in addition a conjugate pad into which the anti-A/anti-B/anti-H conjugated gold particles have been introduced with drying, is so applied that it becomes positioned between the sealing element (adhesive strip) and the indicator zones. Instead of gold particles it is also possible to employ colored polystyrene particles 100 to 400 nm e.g. of Merck Eurolab France/Estapor. Diagonally staggered in the indicator region "blood group determination" positions on the HiFlow Plus 065 membrane dots of 0.2 µl each of the following bonding elements are applied using a dispenser, e.g. AD3200 (Biodot): anti-A antibodies—clone Birma-1 (serologicals, TLJ0105); anti-B antibodies—clone ES-4 (serologicals, NCA0201); anti-AB antibodies—clones AB6, AB26, Ab92 (Medion Diagnostics, 010062); anti-erythrocytes antibodies (rabbit IgG fraction of anti-human RBC, Rockland 209-4139).

In the same manner suspensions of erythrocytes ghosts of the blood group A, B and blood group O (produced from erythrocyte concentrates) are applied in the indicator zone region "serum cross-check" positioned on the HiFlow Plus 140 membrane.

The positioning of the bonding elements of the indicator zone region "serum cross-check" commence with erythrocyte ghosts of the specification blood group A in position x=3 mm/y=10 mm. All other bonding elements are dispensed iterating at distances of x=3 mm/y=1.5 mm from the position of the erythrocyte ghosts of the specification blood group A. The erythrocyte ghosts are dispensed as 0.1-0.5% (v/v) suspensions in 15 mM potassium phosphate buffer pH 7.5, 10% (v/v) methanol.

The positioning of the bonding elements of the indicator zone region "blood group determination" commences with the anti-A antibody in positions x=2.5 mm/y=20 mm. All other bonding elements are dispensed iterating at distances of x=2 mm/y=1.5 mm from the position of the anti-A antibody. The dilutions of the antibody are performed in 15 mM potassium phosphate buffer pH 7.5, 10% (v/v) methanol as follows: anti-A antibody 1:3, anti-B antibody 1:2, anti-AB antibody 1:4, anti-RBC antibody 1:3.

After dispensing the bonding elements the membranes are dried at 40° C. for 20 minutes and subsequently stored at constant air humidity until performance of the test. To the two ends which are distal to the application zone an absorption pad (Schleicher & Schüll, 300) sized 15×15 mm is adhesively bonded to the membrane with a 3 mm overlap. The application zone is separated over the entire membrane width from the remainder of the membrane by the adhesive application of a 1-2 mm wide adhesive strip (Tesa 4124) in position y=5 mm.

Test Batch:

Anti-coagulated complete blood is used as blood samples. For the actual test 100 µl undiluted or blood diluted 1:3 or 1:6 in dilution buffer (EnlisstII, Medion Diagnostics or Diluent 1 DiaMed) is applied to the application zone. Once the blood has left the application zone rinsing is performed twice with 100 µl EnlisstII in order to remove unbound erythrocytes from the membrane.

Result:

(a) Controls: The test is valid if the anti-RBC control (indicator zone region "blood group determination") displays a clearly positive signal (red dot) and if the erythrocyte blood groups O control (indicator zone region "serum cross-check") is stained characteristically purple (gold particles) or in the color of the polystyrene particles used.

(b) Test Results: Depending on the presence or absence of the respective blood group antigens, red dots (positive) or the almost white background coloration of the membrane (negative) are displayed at the respective positions in the indicator zone region "blood group determination". The corresponding isoagglutinines are characterized in the indicator zone region "serum-cross-check" by an absence of the corresponding band. If an isoagglutinine is absent the corresponding band is characteristically stained.

Example 3

Simultaneous Blood Group Determination Serum Cross-Check and Antibody Detection Test on Recipients Production of the Testing Strip:

The testing strip consists of an application zone, an indicator zone region and an absorption region. Membranes of the type Millipore HiFlow Plus 065 are cut to size in strips sized 20 mm×35 mm (width/length; x/y) and adhesively applied onto a support layer (backing sheet e.g. of G&L). Dots of 0.2 µl each of the various bonding elements are applied using a dispenser, e.g. AD3200 (Biodot) digitally staggered in the indicator zone region sub-divided into the indicator zone regions "serum cross-check/antibody detection" (proximal to the application zone) and "blood group determination" (distal to the application zone).

Indicator zone region "serum cross-check/antibody detection"—Suspensions of erythrocyte ghosts of the specification blood group A1, blood group A2, blood group B, blood group O, blood group O Rh-formula $R_1R_1^w$ (detection cell 1), blood group O Rh-formula $R_2R_2$ (detection cell 2), blood group O RH-formula $R_1R_1$ (detection cell 3), as well as anti-human IgG/IgM (goat anti-human IgG, goat anti-human IgM, Signma, I-3382, I-0759) as control; indicator zone region "blood group determination"—anti-A antibody—clone Birma-1 (serologicals, TLJ0105); anti-B antibody-clone ES-4 (serologicals, NCA0201); anti-AB antibodies—(clones AB6, Ab26, AB92 (Medion Diagnostics, 010062); anti-erythrocyte antibodies (rabbit IgG fraction of anti-human RBC, Rockland, 209-4139).

The positioning of the bonding elements of the indicator zone region "serum cross-check" starts with erythrocyte ghosts of the specification blood group A1 in position x=3 mm/y=10 mm, the positioning of the erythrocyte ghosts of the specification blood group A2, B, O follows by iteration at distances of x=2 mm/y=1.5 mm. The positioning of the erythrocyte ghosts of the detector cell 1 proceeds in position x=11 mm/y=10 mm the positioning of the erythrocyte ghosts of the detector cells 2 and 3 as well as the human IgG/IgM iterates at distances of x=2 mm/y=1.5 mm. The erythrocyte ghosts are dispensed as 0.1-0.5% (v/v) suspensions in 15 mM potassium phosphate buffer pH 7.5, 10% (v/v) methanol, the anti-human IgG/IgM antibodies as 1:1 mixture in concentrations of 50 µg/ml in 15 mM potassium phosphate buffer pH 7.5, 10% (v/v) methanol.

The positioning of the binding elements of the indicator zone region "blood group determination" commences with the anti-A antibody in position x=4 mm/y=20 mm. All other bonding elements are dispensed by iteration at distances of x=4 mm/y=1.5 mm to the position of the anti-A antibody. The dilutions of the antibodies take place in 15 mM potassium phosphate buffer pH 7.5, 10% (v/v) methanol as follows: anti-A antibody 1:3, anti-B antibody 1:2, anti-AB antibody 1:4, anti-RBC antibody 1:3.

The membranes, after dispensing the bonding elements, are dried for 20 minutes at 40° C. and subsequently stored at constant air humidity until the test is to be performed. At the end distal to the application zone an absorption pad (Schleicher & Schüll, 300) sized 20×15 mm, is adhesively bonded to the membrane with a 3 mm overlap. The application zone is separated from the remaining membrane over the entire width of the membrane by the adhesive application of an adhesive strip (Tesa 4124) 1-2 mm wide in position y=5 mm.

Test Batch:

Anti-coagulated complete blood is used for the blood samples. For the test proper, 120 µl undiluted blood or blood diluted 1:3 or 1:6 in dilution buffer (EnlisstII, Medion Diagnostics or diluent 1, DiaMed) is applied in the application zone. Once the blood has left the application zone rinsing is performed twice with 120 µl EnlisstII in order to remove unbonded erythrocytes from the membrane. Thereafter 75 µl anti-IgG/A/M conjugated gold particles (20 to 40 nm, Arista Biologicals, CGIGA-0800, CGIGG-0800, CGIGM-0800), 1:10 (v/v) diluted in TBS, 0.08% gelatine, 0.5% albumin, are applied onto the application zone. Instead of the gold particles it is possible also to use colored polystyrene particles 100 to 400 nm e.g. from Merck Eurolab France/Estapor. Once the gold particles have left the application zone, the membrane is once again rinsed once or twice with 120 µl EnlisstII.

Result:

(a) Controls: The test is valid if the anti-RBC control (indicator zone XII, indicator zone region "blood group determination") displays a clearly positive signal (red dot) and if the anti-IgG/IgM control (indicator zone VIII, indicator zone region "serum reverse grouping/antibody test") is stained characteristically purple (gold particles) or in the color of the polystyrene particles used. The anti-IgG/IgM control must in each case be stained so that in the case of a person of blood group AB having no irregular antibodies, the staining of this indicator zone in complete absence of other signals in the indicator zone region "serum reverse grouping/antibody test" confirms a correct test performance. The indicator zone IV (erythrocyte ghosts blood group O) is a negative control for isoagglutinines. A staining of this indicator zone means that besides isoagglutinines also irregular antibodies must be present, i.e. that at least one of the three indicator zones V, VI, VII must likewise be stained. If this is not the case, the test is invalid.

(b) Test results: Depending on the presence or absence of the respective blood group antigens, red dots (positive) or almost white background color (negative) of the membrane are displayed in the respective positions in the indicator zone region "blood group determination". The corresponding isoagglutinines are detectable in the indicator zone region "serum reverse grouping" by the characteristical purple of the gold particles in the form of purple colored dots or in the color of the polystyrene particles used. In the absence of isoagglutinine no signals differing from background are detectable in those positions. If an irregular antibody is present, one, two or all three of the indicator zones which include the erythrocyte ghosts of the detector cells 1, 2 or 3 are stained by the characteristic purple of the gold particles or in the color of the polystyrene particles used.

Example 4

Simultaneous Blood Group Determination, Serum Cross-Check (Reverse Grouping) and Antibody Detection Test for Donor Production of the Test Strip:

In principle the structure of the test strip corresponds to the structure of the test strip in Example 2. The format of the Millipore HiFlow Plus 065 membrane is 15 mm×35 mm (width/length; x/y). The indicator zones of the indicator zone region "blood group determination" correspond to Example 2. In the indicator region "serum cross-check/antibody test" dots of 0.2 µl of the following bonding elements are dispensed using a dispenser, e.g. AD3200 (Biodot):

Suspensions of erythrocytes ghosts of the specification blood group A1, blood group A2, blood group B, blood group O, erythrocyte ghosts of a mixture of the cells to be detected 1-3 (see Example 2) as well as anti-human IgG/IgM (goat anti-human IgG, goat anti-human IgM, Sigma, I-3382, I-0759) serve as controls.

The positioning of the bonding elements of the indicator zone region "serum cross-check/antibody test" commence with erythrocyte ghosts of the specification blood group A1 in position x=2.5 mm/y=10 mm, the positioning of the erythrocyte ghosts of the specification blood group A2, B, O is iterated at distances of x=2 mm/y=1.5 mm. The positioning of the erythrocyte ghosts of the mixture of the cells for detection 1-3 takes place in positions x=10.5 mm/y=13 mm, that of the human IgG/IgM in position x=12.5 mm/y=14.5 mm. The erythrocyte ghosts are dispensed as 0.1-0.5% (v/v) suspensions in 15 mM potassium phosphate buffer pH 7.5, 10% (v/v) methanol, the anti-human IgG/IgM antibodies as 1:1 mixtures in a concentration of 50 µg/ml in 15 mM potassium phosphate buffer pH 7.5, 10% (v/v) methanol.

The positioning of the bonding elements of the indicator zone region "blood group determination" starts with the anti-A antibody in position x=3 mm/y=20 mm. All other bonding elements of the indicator zone are dispensed, iterated at distances of x=3 mm/y=1.5 mm to the position of the anti-A antibody. The dilutions of the antibodies proceed in 50 mM potassium phosphate buffer pH 7.5, 10% (v/v) methanol as follows: anti-A antibody 1:3, anti-B antibody 1:2, anti-AB antibody 1:4, anti-RBC antibody 1:3.

The membranes, after dispensing the bonding elements, are dried for 20 minutes at 40° C. and thereafter stored at constant air humidity until testing takes place. At the end distal to the application zone an absorption pad (Schleicher & Schüll, 300) sized 15×15 mm is adhesively applied overlapping the membrane by 3 mm. The application zone is separated from the remaining membrane by the adhesive application of a 1-2 mm wide test strip (Tesa 4124) in position y=6 mm over the entire membrane width.

Test Batch:
The test batch corresponds to the batch in Example 1.
Result:

(a) Controls: The test is valid if the anti-RBC control (indicator zone X, indicator zone region "blood group determination") displays a clearly positive signal (red dot) or if the anti-IgG/IgM control (indicator zone VI, indicator zone region "serum cross-check/antibody detection") is characteristically purple (gold particles) or is stained in the color of the polystyrene particles used. The anti-IgG/IgM control must in any event be stained so that in the case of a person of blood group AB, who has no irregular antibodies, the staining of this indicator zone in the complete absence of other signals in the indicator zone region "serum cross-check/antibody test" denotes a correct test performance. The indicator zone IV (erythrocyte ghosts blood group O) is a negative control. A staining of this indicator zone denotes, that besides isoagglutinines also irregular antibodies must be present, i.e. that at least one of the three indicator zones V, VI, VII must likewise be stained. If this is not the case the test is invalid.

(b) Test results: Depending on the presence or absence of the respective blood group antigens red dots (positive) or the almost white background coloration of the membrane (negative) are displayed in the respective positions in the indicator zone region. The corresponding isoagglutinines are detectable in the indicator zone region "serum reverse grouping" by the characteristic purple of the gold particles in the form of purple stained dots or in the color of the polystyrene particles used. In the absence of an isoagglutinine no signals differing from background are detectable in those positions. In the presence of an irregular antibody one, two or all three of the indicator zones including the erythrocyte ghosts of the detection cells 1, 2 or 3 are stained by the characteristic purple of the gold particles or in the color of the polystyrene particles used.

Example 5

Simultaneous Blood Group Determination and Detection of Infection Markers

Production of the Tests Strips:
The test strips consist of an application zone, an indicator zone region and a absorption region. Membranes of the type Millipore HiFlow Plus 065 are cut to size to 15 mm×35 mm dimensions (width/length; x/y) and are adhesively bonded onto a support layer (backing sheet e.g. of G&L). In the indicator region sub-divided into the indicator zone region "detection of infection markers" (proximal to the application zone) and "blood group determination" (distal to the application zone) dots, each 0.2 µl, of the various bonding elements are applied diagonally staggered using a dispenser, e.g. AD3200 (Biodot):

Indicator zone region "detection of infection markers"—solutions of the recombinant antigens (Syphilis; TpN 15, TpN 17, TpN 47), synthetic peptides of sequences of the glycoproteins gp-14, gp-41 (HIV-1; HIV-0) and gp-36 (HIV-2) recombinant HCV antigens (C-100, C-200, C33c, C22), monoclonal antibodies (HBsAg) as well as anti-human IgG/IgM (goat anti-human IgG, goat anti-human IgM, Sigma, I-3382, I-0759) as controls; indicator zone region "blood group determination"—anti-A antibodies—clone Birma-1 (serologicals, TLJ0105); anti-B antibodies—clone ES-4 (serologicals, NCA0201); anti-AB antibodies—clones AB6, AB26, AB92 (Medion Diagnostics, 010062); anti-D antibodies—clones LDM3/ESD1 (SNBTS), anti-CDB antibodies—clones MS-24/MS-201/MS 80/MS-258 (serologicals), anti-erythrocyte antibodies (rabbit IgG fraction of anti-human RBC, Rockland, 209-4139).

The positioning of the bonding elements of the indicator zone region "detection of infection markers" commences with synthetic peptides of the specificity HIV-1 (gp-14, gp-41) in position x=2.5 mm/y=10 mm. All other bonding elements are dispensed, iterating at distances of x=2 mm/y=1.5 mm to the position of the indicator zone I. The bonding elements of the indicator zones I-V are dispensed in suitable concentrations in 15 mM potassium phosphate buffer pH 7.5, 10% (v/v) methanol, the anti-human IgG/IgM antibodies in a concentration of 50 µg/ml in 15 mM potassium phosphate buffer pH 7.5, 10% (v/v) methanol.

The positioning of the bonding elements of the indicator zone region "blood group determination" commence with the anti-A antibody in position x=2.5 mm/y=20 mm. All other bonding elements of the indicator zone region are iterating at distances of x=2 mm/y=1.5 mm to the position of the anti-A antibody. The dilutions of the antibodies proceed in 15 mM potassium phosphate buffer pH 7.5, 10% (v/v) methanol as follows: anti-A antibody 1:3; anti-B antibody 1:2; anti-AB antibody 1:4; anti-RBC antibody 1:3.

The membranes, after the dispensing of the bonding elements, are dried for 20 minutes at 40° C. and subsequently stored at constant air humidity until testing is performed. At the end distal to the application zone, an absorption pad (Schleicher & Schüll, 300), sized 15×15 mm, is adhesively applied to the membrane with a 3 mm overlap. The application zone is separated from the remaining membrane over the entire membrane width by the adhesive application of a 1-2 mm wide adhesive strip (Tesa 4124) in position y=6 mm.

Test Batch:

As blood samples anti-coagulative complete blood lots are used. For the test proper blood is applied into the application zone either undiluted or diluted 1:3 or 1:6 in dilution buffer (EnlisstII, Medion Diagnostics or diluent 1, DiaMed). Once the blood has left the application zone rinsing proceeds twice with 100 µl EnlisstII in order to rinse unbound erythrocytes from the membrane.

Therafter, 50 µl of a mixture of anti-IgG/A/M conjugated gold particles (20 to 40 nm, Arista Biologicals, CGIGA-0800, CGIGG-0800, CGIGM-0800), diluted 1:10 (v/v) in TBS, 0.08% gelatine, 0.5% albumin as well anti-HbsAg conjugated gold particles (Arista Biologicals, ABHBS-0500) are applied in suitable dilution onto the application zone. Instead of the gold particles it is also possible to use colored, 100 to 400 nm polystyrene particles, e.g. from Merck Eurolab France/Estapor. Once these have left the application zone the membranes are once again rinsed once or twice with 100 µl EnlisstII.

Result:

The test is valid if the anti-RBC control (indicator zone XII, indicator zone region "blood group determination") displays a clearly positive signal (red dot) and if the anti-IgG/IgM control (indicator zone VI, indicator zone region "detection of infection markers") is characteristically purple (gold particles) or is stained in the color of the polystyrene particles used. Depending on the presence or absence of the respective blood group antigens, red dots (positive) or the nearly white background coloration of the membrane (negative) appear in the respective positions. In the presence of antibodies against HIV-1, HIV-2, Syphilis or of Hepatitis B surface antigen (HBsAg) the respective position is detectable as purple colored dots due to the characteristically purple staining by the gold particles. If polystyrene particles have been used as indicator particles the respective position is stained in the color of the polystyrene particles used. In the by far most frequent situation, namely a negative reaction for all infection markers, only the anti-IgG/IgM control (indicator zone VI, indicator zone region "detection of infection markers") is stained.

Example 6

Simultaneous Blood Group Determination and Detection of Antibodies Against Thrombocytal Antigens Production of the Test Strip:

In principle the structure and the format of the test strip corresponds to the test strip structure in Example 4. The indicator zone region is sub-divided into the indicator zone regions "blood group determination" and "detection of antibodies against thrombocyte antigens". 0.2 µl dots of the following bonding elements are dispensed using a dispenser, e.g. AD3200 (Biodot):

Indicator zone region "detection of antibodies against thromocytal antigens"—membrane proteins of thrombocytes of blood group O having distinctive HPA antigen profiles such as HPA 1bb3aa5bb and HPA 1aa3bb5aa as well as anti-human IgG/IgM (goat anti-human IgG, goat anti-human IgM, Sigma, I-3382, I-0759) as controls; indicator zone region "blood group determination"—anti-A antibodies—clone Birma-1 (serologicals, TLJ0105); anti-B antibodies—clone ES-4 (serologicals, NCA0201); anti-AB-clones AB6, AB26, AB92 (Medion Diagnostics, 010062); anti-D antibodies— clones LDM3/ESD1 (SNBTS), anti-CDE antibodies— clones MS-24/MS-201/MS 80/MS-258 (serologicals), anti-erythrocyte antibodies (rabbit IgG fraction of anti-human RBC, Rockland, 209-4139). As alternatives to the membrane proteins of the thrombocyte it is also possible to apply recombinant antigens having the corresponding characteristic features (HPA-antigen profile).

The positioning of the bonding elements of the indicator zone region "detection of antibodies against thrombocytal antigens" commences with membrane proteins antigens profile HPA 1bb3aa5bb in position x=4 mm/y=10 mm. All other bonding elements are dispensed iterating at distances of x=3.5 mm/y=2 mm to the position of the indicator zone I. The bonding elements of the indicator zones I and II are dispensed in suitable concentrations in 15 mM potassium phosphate buffer pH 7.5, 10% (v/v) methanol, and the anti-human IgG/IgM antibodies in a concentration of 15 µg/ml in 15 mM potassium phosphate buffer pH 7.5, 10% (v/v) methanol.

The positioning of the bonding elements of the indicator zone region "blood group determination" corresponds to Example 4.

The membranes, after dispensing the bonding elements, are dried for 20 minutes at 40° C. and subsequently stored at constant air humidity until testing takes place. At the end distal to the application zone, an absorption pad (Schleicher & Schüll, 300), sized 15×15 mm is adhesively applied to the membrane with a 3 mm overlap. The application zone is separated from the remainder of the membrane over the entire membrane's width by the adhesive application of a 1-2 mm wide adhesive strip (Tesa 4124) in position y=6 mm.

Test Batch:

Anti-coagulated complete blood lots are used for the blood samples. For the test proper 100 µl of blood, undiluted or diluted 1:3 or 1:6 in dilution buffer (EnlisstII, Medion Diagnostics or diluent 1, DiaMed) are applied to the application zone. Once the blood has left the application zone rinsing is performed twice with 100 µl EnlisstII in order to rinse unbound erythrocytes from the membrane.

Thereafter 50 µl of a mixture of anti-IgG/A/M conjugated gold particles (20 to 40 nm, Arista Biologicals, CGIGA-0800, CGIGG-0800, CGIGM-0800), diluted 1:10 (v/v) in TBS, 0.08% gelatine, 0.5% albumin are applied to the application zone. Instead of gold particles it is also possible to use colored, 100 to 400 nm polystyrene particles, e.g. from Merck Eurolab France/Estapor. Once the gold particles have left the application zone the membrane is rinsed again once or twice with 100 µl EnlisstII.

Result:

The test is valid if the anti-RBC control (indicator zone IX, indicator zone region "blood group determination") displays a clear positive signal (red dot) and if the anti-IgG/IgM control (indicator zone III, indicator zone region "detection of antibodies against thrombocytal antigens") is stained characteristically purple (gold particles) or in the color of the polystyrene particles used. Depending on the presence or absence of the respective blood group antigens, red dots (positive) or the almost white background coloration of the membrane (negative) are displayed in the respective positions. In the presence of antibodies against thrombocytal antigens the respective position is recognizable by the purple staining characteristic for gold particles and as a purple colored spot. If polystyrene particles are used as indicator particles the respective position is stained in the color of the polystyrene particles used.

Having described the invention, we now claim the following and their equivalents:

1. A device for the simultaneous and qualitative or quantitative determination of a plurality of analytes, wherein at least one of the plurality of analytes is a cellularly bonded analyte, in a liquid sample, the device comprising:
   a single membrane with an application zone for the application of the liquid sample,
   at least one group of at least two indicator zones, which are able to interact with the analytes, and
   at least one absorption region which takes up the liquid after having passed the indicator zones;
   wherein the indicator zones are located between the application zone and the absorption region;
   wherein the at least two indicator zones are positioned on the membrane substantially parallel and absent a physical divider between indicator zones, the at least two indicator zones comprise at least two types of indicator particles of which at least one type being erythrocytes; and
   wherein the at least two indicator zones comprise a first indicator zone containing a bonding element for binding the cellularly bound analyte and the at least two indicator zones comprise a second indicator zone containing a binding element for binding an analyte comprising an erythrocyte in the liquid sample, wherein the erythrocyte serves as both the indicator particle and the analyte.

2. The device according to claim 1, wherein the indicator zones are so arranged that the test liquids flow through not more than one indicator zone.

3. The device according to claim 1, wherein the indicator zones are arranged in a V-, W-, M-, N-shape or a linear row.

4. The device according to claim 1, wherein at least two rows of indicator zones are arranged in the flow direction, one behind the other and/or laterally staggered, and the indicator zones of each row are arranged in relation to one another with a gap there between so that the test liquid for any one flow track flows through not more than one indicator zone.

5. The device according to claim 1, wherein at least two rows of indicator zones are arranged in the flow direction one behind the other and/or side by side and the indicator zones of each row in relation to one another are arranged without a gap there between so that the test liquid for any one flow track passes through more than one indicator zone.

6. The device according to claim 1, wherein at least two groups of indicator zones are arranged which are disposed starting from the application zone in different flow directions.

7. The device according to claim 1, wherein the indicator zones comprise antibodies or antibody fragments or lectines, antigens or antigen epitopes, cells or cell fragments, or mixtures thereof.

8. The device according to claim 1, wherein the indicator zones comprise antibodies or antibody fragments against blood group antigens or antigen epitopes and membranes or cell fragments of blood groups A1, A2, B, O erythrocytes, or mixtures thereof.

9. The device according to claim 1, wherein the indicator zones comprise antibodies or antibody fragments against blood group antigens or antigen epitopes and synthetic peptides, recombinant antigens, antibodies or antibody fragments against infective markers, or mixtures thereof.

10. The device according to claim 1, wherein the indicator zones comprise antibodies or antibody fragments against blood group antigens or antigen epitopes and fragments of thrombocytes, lymphocytes, or mixtures thereof.

11. The device according to claim 1, wherein the membrane consists of polyethylene, nitrocellulose or nylon.

12. The device according to claim 1, wherein downstream of the application zone and upstream of the indicator zones at least one sealing element is provided on the membrane.

13. The device according to claim 12, wherein downstream of the sealing element and upstream of the indicator zones at least one conjugate pad is applied.

14. The device according to claim 1, wherein the components of the device have been applied onto a support layer for mechanical reinforcement.

15. The device according to claim 1, wherein the components of the device are integrated in a casing.

16. The device according to claim 1, comprising at least two groups of indicator zones and at least two absorption regions, wherein the application zone is positioned in the central region of the membrane.

* * * * *